(12) United States Patent
Crowley et al.

(10) Patent No.: US 7,947,679 B2
(45) Date of Patent: May 24, 2011

(54) FUNGICIDES

(75) Inventors: Patrick Jelf Crowley, Berkshire (GB); Markus Dobler, Cambridge, MA (US); Urs Mueller, Basel (CH); John Williams, Berkshire (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 440 days.

(21) Appl. No.: 10/540,037

(22) PCT Filed: Dec. 3, 2003

(86) PCT No.: PCT/GB03/05248
§ 371 (c)(1), (2), (4) Date: Jun. 22, 2005

(87) PCT Pub. No.: WO2004/056824
PCT Pub. Date: Jul. 8, 2004

(65) Prior Publication Data
US 2006/0069089 A1    Mar. 30, 2006

(30) Foreign Application Priority Data
Dec. 23, 2002   (GB) ................................. 0230018.4

(51) Int. Cl.
A61K 31/44    (2006.01)
A61K 31/535   (2006.01)
C07D 471/02   (2006.01)

(52) U.S. Cl. ................ 514/234.2; 514/253.02; 514/300; 546/122

(58) Field of Classification Search .................. 546/122; 514/300, 234.2, 253.02
See application file for complete search history.

(56) References Cited

U.S. PATENT DOCUMENTS

| | | | |
|---|---|---|---|
| 3,984,412 A | 10/1976 | Denzel et al. | |
| 4,801,592 A | 1/1989 | Graf et al. | |
| 5,258,356 A | 11/1993 | Saupe et al. | |
| 5,597,776 A | 1/1997 | Bratz et al. | |
| 5,602,142 A * | 2/1997 | Papadopoulou-Rosenzweig et al. | 514/290 |
| 5,821,244 A | 10/1998 | Schaper et al. | |
| 5,852,042 A | 12/1998 | Jakobi et al. | |
| 5,955,473 A | 9/1999 | Wagner et al. | |
| 6,117,884 A | 9/2000 | Daeuble et al. | |
| 6,962,917 B2 * | 11/2005 | Davies et al. | 514/248 |

FOREIGN PATENT DOCUMENTS

| | | |
|---|---|---|
| EP | 0410762 | 1/1991 |
| EP | 0537463 | 4/1993 |
| EP | 1249452 | 10/2002 |
| WO | WO 92/07468 | 5/1992 |
| WO | WO 92/22533 | 12/1992 |
| WO | WO 93/13097 | 7/1993 |
| WO | 0117972 A2 | 3/2001 |
| WO | WO 02/051845 | 7/2002 |
| WO | WO 02/083676 | 10/2002 |
| WO | WO 02/083677 | 10/2002 |
| WO | WO 02/088125 | 11/2002 |
| WO | WO 02/088126 | 11/2002 |
| WO | WO 02/088127 | 11/2002 |
| WO | 2004056825 | 7/2004 |
| WO | 2004056826 | 7/2004 |
| WO | 2004056829 | 7/2004 |

OTHER PUBLICATIONS

Mogilaiah, K., et al., "LiCl Catalyzed Claisen-Schmidt Condensation in Solvent-Free Conditions Using Microwaves", Synthetic Communications, vol. 33, No. 1, pp. 73-78 (2003).
Mogilaiah, K., et al., "Microwave assisted Claisen-Schmidt Condensation Under Solvent Free Conditions", Indian Journal of Chemistry, vol. 41B, Oct. 2002, pp. 2194-2196.
Badawneh, M., et al., "Synthesis of varioulsy Substituted 1,8-naphthyridine derivatives and evaluation of their antimycobacterial activity"; Farmaco 57 (2002) pp. 631-639.
Ferrarini, P., et al., "Synthesis and Antiplatelet Activity of Some 2,7-di(N-cycloamino)-3-phenyl-1,8-naphthyridine Derivatives"; Farmaco 56 (2001), pp. 311-318.
Ferrarini, P., et al., "Synthesis and Antiplatelet Activity of some 3-phenyl-1,8-naphthyridine Derivatives"; Farmaco 55 (2000), pp. 603-610.
Dornow, A. and Loh, J., "Uber Synthesen and Umsetzungen von 1,8-Naphthyridinen"; Arch. Pharm., (1957), pp. 136-153.
Ferrarini, P., et al., "Preparazione Ed Esame Farmacologico Di Alcuni Derivati 1,8-Naftiridin-4-Idrazonici"; Farmaco, Edizione Scientifica (1979) pp. 165-169.
Flowers, W., et al., "Reaction of Aromatic or Heterocyclic Amines and Perfluoro-2-methylpent-2-ene to give Fused Pyridines, ..."; Journal of the Chemical Society (1974); 134.
Beccalli, E. et al, "Rearrangement reactions of 5-aminio-1-(2-formyl-,-benzoyl-,-cyanoaryl)..."; Journal of the Chemical Society, PerkinTransactions 1 (1996), (12), p. 1359.
Pokorny, D., et al, "The Meisenheimer Reaction of the 1,X-Naphthyridine 1-Oxides"; Journal of Organic Chemistry (1972), 37(2), pp. 3101-3105.
Hawes, E., et al., "2,3-Disubstituted 1,6-Naphthyridines as Potential Diuretic Agents"; Journal of Medicinal Chemistry, (1973); 16(7), p. 849.
Roma, G., et al., "1,8-Naphthyridines IV. 9-Substituted N,N-dialkyl-5-(alkylaminio or cycloalkylamino) [1,2,4]..."; European Journal of Medicinal Chemistry,(200), 35(11) 1021-.
Toja, E., et al., "Pyrrolopyridine Analgos of Nalidixic Acid, 1. Pyrrolo[2,3 b]pyridines"; J. Heterocyclic Chemistry, 23, p. 1555 (1986).

(Continued)

Primary Examiner — Sabiha Qazi
(74) Attorney, Agent, or Firm — Rebecca A. Howard

(57) ABSTRACT

The naphthyridine derivatives of formula (I) a and method of combating or controlling phytopathogenic fungi which comprises applying the compounds of formula (I) to a plant, to a seed of a plant and to the locus of the plant.

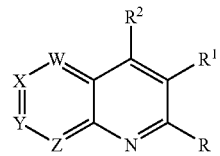

(I)

11 Claims, No Drawings

OTHER PUBLICATIONS

Schafer, H., et al., "Zur Synthese von 4-Aminochinolinen und-chinolinonen-(2) aus Anthranilsaurenitril"; J.f.prakt. Chemie, 321(4), 695 (1970).

Bredereck, H., et al, "Synthesen von Pyrido[2.3-d]pyrimidinen"; Chem. Ber. 96, 1868-1872, (1963).

Jian-Long Chen et al.: "Synthesis of Some Benzufuronaphthyridines and Benzofuronaphthyridine Derivatives", Journal of Heterocyclic Chemistry, vol. 30, No. 3, 1993, pp. 909-912. p. 909, compounds 2a, 2b, 3a, 3b.

A. Dornow et al.: "Uber Synthesen and Umsetzungen von 1,8-Naphthyridinen" Archiv Der Pharmazie, vol. 62, No. 3, 1957, pp. 136-153.

Dornow A et al: "Uber Ortho-Kondensationen Heterocyclischer O-Amino-Carbonaure—Derivative", Chemische Berichte, Verlag Chemie (GMBH, Weinhim, DE, vol. 91, No. 9, 1958, pp. 1834-1840, XP000561883, p. 1840, compounds XXIII, XXIV, XXV.

Database Chemcats "Online!, Chemical Abstract Service, Columbus, Ohio, US: Database Accession No. 2002:2623896 XP002271641, order No. AK-986/11842185 & "Interchim Intermediates", Jul. 9, 2002.

J. Med. Chem. (1983), 26(3), 403.

Database Beilstein; Beilstein Institute for Organic Chemistry, Frankfurt-Main, DE; Database Accession No. 538395 (BRN) & CROAT. CHEM. ACTA, vol. 44, 1972, pp. 419-421.

Med. Chem. (1968), 11(6), 1216-18.

J. Med. Chem. (1970), 13(5), 853-7.

Eur. J. Med. Chem.-Chim. Ther. (1980), 15, 269.

* cited by examiner

FUNGICIDES

This application is a 371 of International Application No. PCT/GB2003/005248 filed 3 Dec., 2003, which claims priority to GB 0230018.4, filed Dec. 23, 2002, the contents of which are incorporated herein by reference.

This invention relates to novel derivatives of naphthyridines, to processes for preparing them, to certain intermediate chemicals used in their manufacture, to compositions containing them and to methods of using them to combat fungi, especially fungal infections of plants.

Derivatives of the nitrogen-containing 5,6 ring system s-1,2,4-triazolo[1,5-a]pyrimidine are known from the patent literature as being useful for controlling phytopathogenic fungi. Examples of recent patent publications include EP-A-1249452, WO 02/051845, WO 02/083676, WO 02/083677, WO 02/088125, WO 02/088126, WO 02/088127. The plant fungicidal activity of certain derivatives of naphthyridines is described in EP-A-0410762 and U.S. Pat. No. 4,801,592. Other naphthyridine derivatives are described, for example, in WO 92/07468 and U.S. Pat. No. 5,258,356 as herbicides and in WO 93/13097 and WO 92/22533 for pharmaceutical applications. Naphthyridine derivatives are also known in the general chemical literature, for example, from *Synthetic Communications* (2003), 33(1), 73; *Indian Journal of Chemistry*, Section B (2002), 41B (10), 2194; *Farmaco* (2002), 57(8), 631; *Farmaco* (2001), 56(4), 311; *Farmaco* (2000), 55(9-10), 603; *Arch. Pharm.* (1957), 290, 136; *Farmaco, Edizione Scientifica* (1979), 34(2), 165; *Journal of the Chemical Society*, Chemical Communications (1974), (4), 134; *Journal of the Chemical Society*, Perkin Transactions 1 (1996), (12), 1359; *Journal of Organic Chemistry* (1972), 37(20), 3101; *Journal of Medicinal Chemistry* (1973), 16(7), 849; *Journal of the Chemical Society*, Chemical Communications (1974), (4), 134; and the *European Journal of Medicinal Chemistry* (200), 35(11), 1021-1035.

The present invention is concerned with the provision of alternative, novel naphthyridines for combating phytopathogenic diseases on plants and harvested food crops.

Thus, according to the present invention, there is provided a compound of the general formula (1):

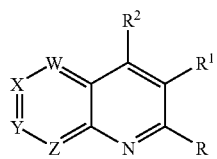

(1)

wherein
one of W, X, Y and Z is N and the others are $CR^8$;
$R^8$ is H, halo, $C_{1-4}$ alkyl, $C_{1-4}$ alkoxy or halo($C_{1-4}$)alkyl, provided that when X is CH, Z is N, R is $NHNH_2$, $R^1$ is phenyl and $R^2$ is Cl, W and Y are not both $CCH_3$;
one of R and $R^2$ is $NR^3R^4$ and the other is halo, $C_{1-8}$ alkyl, $C_{1-8}$ alkoxy, $C_{1-8}$ alkylthio, $C_{2-8}$ alkenyl, $C_{2-8}$ alkynyl or cyano;
$R^1$ is aryl, heteroaryl, morpholino, piperidino or pyrrolidino;
$R^3$ and $R^4$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl($C_{1-6}$)alkyl, heteroaryl, heteroaryl($C_{1-8}$)alkyl, $NR^5R^6$, provided that not both $R^3$ and $R^4$ are H or $NR^5R^6$, or
$R^3$ and $R^4$ together form a $C_{3-7}$ alkylene or $C_{3-7}$ alkenylene chain optionally substituted with one or more $C_{1-4}$ alkyl or $C_{1-4}$ alkoxy groups, or, together with the nitrogen atom to which they are attached, $R^3$ and $R^4$ form a morpholine, thiomorpholine, thiomorpholine S-oxide or thiomorpholine S-dioxide ring or a piperazine or piperazine N—($C_{1-4}$)alkyl (especially N-methyl) ring; and $R^5$ and $R^6$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl ($C_{1-6}$)alkyl, heteroaryl or heteroaryl($C_{1-8}$)alkyl;

any of the foregoing alkyl, alkenyl, alkynyl or cycloalkyl groups or moieties (other than for $R^8$) being optionally substituted with halogen, cyano, $C_{1-6}$ alkoxy, $C_{1-6}$ alkylcarbonyl, $C_{1-6}$ alkoxycarbonyl, $C_{1-6}$ haloalkoxy, $C_{1-6}$ alkylthio, tri($C_{1-4}$)alkylsilyl, $C_{1-6}$ alkylamino or $C_{1-6}$ dialkylamino, any of the foregoing morpholine, thiomorpholine, piperidine, piperazine and pyrrolidine rings being optionally substituted with $C_{1-4}$ alkyl (especially methyl), and any of the foregoing aryl or heteroaryl groups or moieties being optionally substituted with one or more substituents selected from halo, hydroxy, mercapto, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, halo($C_{1-6}$)alkyl, halo($C_{1-6}$)alkoxy, $C_{1-6}$ alkylthio, halo($C_{1-6}$)alkylthio, hydroxy($C_{1-6}$)alkyl, $C_{1-4}$ alkoxy($C_{1-6}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR'''' or —N=CR'''R'''', in which R''' and R'''' are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

The invention includes a compound of the general formula (1) as defined immediately above except that: $C_{1-8}$ alkoxy and $C_{1-8}$ alkylthio are excluded as values of R and $R^2$; $C_7$ alkylene and $C_{3-7}$ alkenylene are excluded as chains formed by $R^3$ and $R^4$; the $C_{3-6}$ chain that $R^3$ and $R^4$ may form may only be optionally substituted with one or more methyl groups; thiomorpholine, thiomorpholine S-oxide, thiomorpholine S-dioxide and piperazine are excluded as rings that $R^3$ and $R^4$ may form; tri($C_{1-4}$)alkylsilyl is excluded as a substituent of any alkyl, alkenyl, alkynyl or cycloalkyl group or moiety and any morpholine, piperidine or pyrrolidine ring is unsubstituted.

The compounds of the invention may contain one or more asymmetric carbon atoms and may exist as enantiomers (or as pairs of diastereoisomers) or as mixtures of such. They may also exist as diastereoisomers by virtue of restricted rotation about a bond. However, mixtures of enantiomers or diastereoisomers may be separated into individual isomers or isomer pairs, and this invention embraces such isomers and mixtures thereof in all proportions. It is to be expected that for any given compound, one isomer may be more fungicidally active than another.

Except where otherwise stated, alkyl groups and alkyl moieties of alkoxy, alkylthio, etc., contain from, to 8, suitably from 1 to 6 and typically from 1 to 4, carbon atoms in the form of straight or branched chains. Examples are methyl, ethyl, n- and iso-propyl, n-, sec-, iso- and tert-butyl, n-pentyl and n-hexyl. Cycloalkyl groups contain from 3 to 8, typically from 3 to 6, carbon atoms and include bicycloalkyl groups such as the bicyclo[2.2.1]heptyl group. Haloalkyl groups or moieties are typically trichloromethyl or trifluoromethyl or contain a trichloromethyl or trifluoromethyl terminal group.

Except where otherwise stated, alkenyl and alkynyl moieties also contain from 2 to 8, suitably from 2 to 6 and typically from 2 to 4, carbon atoms in the form of straight or branched chains. Examples are allyl, 2-methylallyl and propargyl. Optional substituents include halo, typically fluoro. An example of halo-substituted alkenyl is 3,4,4-trifluoro-n-butenyl.

Halo includes fluoro, chloro, bromo and iodo. Most commonly it is fluoro, chloro or bromo and usually fluoro or chloro.

Aryl is usually phenyl but also includes naphthyl, anthryl and phenanthryl.

Heteroaryl is typically a 5- or 6-membered aromatic ring containing one or more O, N or S heteroatoms, which may be fused to one or more other aromatic or heteroaromatic rings, such as a benzene ring. Examples are thienyl, furyl, pyrrolyl, isoxazolyl, oxazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuryl, benzothienyl, dibenzofuryl, benzothiazolyl, benzoxazolyl, benzimidazolyl, indolyl, quinolinyl and quinoxalinyl groups and, where appropriate, N-oxides thereof.

The 6,6-ring systems embraced by the general formula (1) are 1,8-naphthyridines (where W, X and Y are all $CR^8$ and Z is N), 1,7-naphthyridines (where W, X and Z are all $CR^8$ and Y is N), 1,6-naphthyridines (where W, Y and Z are all $CR^8$ and X is N) and 1,5-naphthyridines (where X, Y and Z are all $CR^8$ and W is N). Of particular interest are 1,8-naphthyridines.

$R^8$, which may be the same or different for the three $CR^8$ values of W, X, Y and Z, is H, halo (for example bromo), $C_{1-4}$ alkyl (for example methyl), $C_{1-4}$ alkoxy (for example methoxy) or halo($C_{1-4}$)alkyl (for example trifluoromethyl). Usually $R^8$ will be H. However, of particular interest are compounds containing a 3-bromo-1,8-naphthyridine ring (i.e. where W and Y are CH, X is CBr and Z is N).

One of R and $R^2$, preferably $R^2$, is $NR^3R^4$. The other is typically halo, especially chloro or fluoro. In the case of the 1,8-naphthyridine ring system, the more active compounds are those where $R^2$ is $NR^3R^4$. $R^3$ is typically $C_{1-8}$ alkyl (for example ethyl, n-propyl, n-butyl, sec-butyl (the S- or R-isomer or the racemate) and tert-butyl), halo($C_{1-8}$)alkyl (for example 2,2,2-trifluoroethyl, 2,2,2-trifluoro-1-methylethyl (the S- or R-isomer or the racemate), 3,3,3-trifluoropropyl and 4,4,4-trifluorobutyl), hydroxy($C_{1-8}$)alkyl (for example hydroxyethyl), $C_{1-4}$ alkoxy($C_{1-8}$)alkyl (for example methoxymethyl and methoxy-iso-butyl), $C_{1-4}$ alkoxyhalo-($C_{1-8}$) alkyl (for example 2-methoxy-2-trifluromethylethyl), tri($C_{1-4}$)alkylsilyl($C_{1-6}$)alkyl (for example trimethylsilylmethyl), $C_{1-4}$ alkylcarbonyl($C_{1-8}$)alkyl (for example 1-acetylethyl and 1-tert-butylcarbonylethyl), $C_{1-4}$ alkylcarbonylhalo ($C_{1-8}$)alkyl (for example 1-acetyl-2,2,2-trifluoroethyl), phenyl$_{(1-4)}$alkyl (for example benzyl), $C_{2-8}$ alkenyl (for example allyl and methylallyl), halo($C_{2-8}$)alkenyl (for example 3-methyl-4,4-difluorobut-3-enyl), $C_{2-8}$ alkynyl (for example propargyl), $C_{3-8}$ cycloalkyl (for example cyclopropyl, cyclobutyl, cyclopentyl and cyclohexyl) optionally substituted with chloro, fluoro or methyl, $C_{3-8}$ cycloalkyl($C_{1-4}$)-alkyl (for example cyclopropylmethyl, cyclobutylmethyl, cyclopentylmethyl and cyclohexylmethyl), phenylamino, piperidino or morpholino, the phenyl ring of phenylalkyl or phenylamino being optionally substituted with one, two or three substituents selected from halo (typically fluoro, chloro or bromo), $C_{1-4}$ alkyl (typically methyl), halo($C_{1-4}$)alkyl (typically trifluoromethyl), $C_{1-4}$ alkoxy (typically methoxy) and halo($C_{1-4}$)alkoxy (typically trifluoromethoxy). $R^4$ is typically H, $C_{1-4}$ alkyl (for example ethyl and n-propyl), halo (Cl$_4$)-alkyl (for example 2,2,2-trifluoroethyl) or amino. Alternatively $R^3$ and $R^4$ together form a $C_{4-6}$ alkylene chain optionally substituted with methyl, for example 3-methylpentylene, or, together with the nitrogen atom to which they are attached, $R^3$ and $R^4$ form a morpholine, thiomorpholine, thiomorpholine S-oxide or thiomorpholine S-dioxide ring or a piperazine or piperazine N—($C_{1-4}$)alkyl (especially N-methyl) ring, in which the morpholine or piperazine rings are optionally substituted with methyl.

Typically $R^1$ is phenyl optionally substituted with from one to five halogen atoms, particularly fluorine and chlorine atoms and especially fluorine atoms or with from one to three substituents selected from halo (for example fluoro and chloro), $C_{1-4}$ alkyl (for example methyl), halo($C_{1-4}$)alkyl (for example trifluoromethyl), $C_{1-4}$ alkoxy (for example methoxy) or halo($C_{1-4}$)alkoxy (for example trifluoromethoxy). Examples are 2,6-difluorophenyl, 2-fluoro-6-chlorophenyl, 2,5,6-trifluorophenyl, 2,4,6-trifluorophenyl, 2,6-difluoro-4-methoxyphenyl, pentafluorophenyl, 2-fluorophenyl, 2,3,5,6-tetrafluorophenyl, 2-chloro-4,6-difluorophenyl, 2-chlorophenyl, 2,6-dichlorophenyl, 2,4-dichlorophenyl, 2,4,6-trichlorophenyl, 2,3,6-trichlorophenyl, pentachlorophenyl, 2-fluoro-4,6-dichlorophenyl, 4-fluoro-2,6-dichlorophenyl, 2-bromophenyl, 2-fluoro-6-bromophenyl, 2-bromo-4,6-difluorophenyl, 2-fluoro-6-methylphenyl, 2-chloro-6-methylphenyl, 2-methoxyphenyl, 2,6-dimethoxyphenyl, 2-fluoro-6-methoxyphenyl, 2-trifluoromethylphenyl, 2-fluoro-6-trifluoromethylphenyl, 2,6-di-(trifluoromethyl)phenyl, 2-chloro-6-trifluoromethylphenyl, 2,4-difluoro-6-trifluoromethylphenyl, 2,4-difluoro-6-methoxyphenyl and 2,4-difluoro-6-methylphenyl.

Also of particular interest are compounds where $R^1$ is pyridyl optionally substituted with from one to four halogen atoms or with from one to three substituents selected from halo (for example fluoro and chloro), $C_{1-4}$ alkyl (for example methyl), halo(CIA)alkyl (for example trifluoromethyl), $C_{1-4}$ alkoxy (for example methoxy) or halo($C_{1-4}$)alkoxy (for example trifluoromethoxy). Examples are 2,4-difluoropyrid-3-yl, 3,5-difluoropyrid-4-yl, tetrafluoropyrid-4-yl, 3-fluoropyrid-2-yl, 4-fluoropyrid-3-yl, 3-fluoropyridyl, 2-fluoropyrid-3-yl, 2,4,6-trifluoropyrid-3-yl, 3,5-difluoropyrid-2-yl, 2,6-difluoropyrid-3-yl, 2,4-difluoro-6-methoxypyrid-3-yl, 2-fluoro-4-chloropyrid-3-yl, 3-fluoro-5-chloropyrid-4-yl, 2-chloro-4-fluoropyrid-3-yl, 2,4-dichloropyrid-3-yl, 3-chloropyrid-2-yl 1,4-chloropyrid-3-yl, 3-chloropyrid-4-yl, 2-chloropyrid-3-yl, 3-trifluoromethylpyrid-2-yl, 4-trifluoromethylpyrid-3-yl, 3,5-dichloropyrid-2-yl, 4,6-dichloropyrid-3-yl, 3-trifluoromethylpyrid-4-yl, 2-trifluoromethylpyrid-3-yl, 2-fluoro-4-trifluoromethylpyrid-3-yl, 2-fluoro-5-trifluoromethylpyrid-4-yl, 4-fluoro-2-trifluoromethylpyrid-3-yl, 2,6-dichloropyrid-3-yl, 3,5-dichloropyrid-4-yl, 3-chloro-6-trifluoromethylpyrid-2-yl, 3-fluoro-6-trifluoromethylpyrid-2-yl, pyrid-2-yl, pyrid-3-yl and pyrid-4-yl.

Also of particular interest are compounds where $R^1$ is 2- or 3-thienyl optionally substituted with from one to three halogen atoms or with from one to three substituents selected from halo (for example fluoro and chloro), $C_{1-4}$ alkyl (for example methyl), halo-($C_{1-4}$)alkyl (for example trifluoromethyl), $C_{1-4}$ alkoxy (for example methoxy) or halo($C_{1-4}$)-alkoxy (for example trifluoromethoxy). Examples are 3-fluorothien-2-yl, 3-chlorothien-2-yl, 2,4-difluorothien-3-yl, 2,4-dichlorothien-3-yl and 2,4,5-trichlorothien-3-yl.

Examples of other values of $R^1$ of especial interest are unsubstituted piperidino and morpholino, 2-methylpiperidino, 2,6-dimethylpiperidino and 2,6-dimethylmorpholino.

In one aspect the invention provides a compound of the general formula (1) wherein one of W, X, Y and Z is N and the others are $CR^8$;
$R^8$ is H, halo, $C_{1-4}$ alkyl, $C_{1-4}$ alkoxy or halo($C_{1-4}$)alkyl, provided that when X is CH, Z is N, R is $NHNH_2$, $R^1$ is phenyl and $R^2$ is Cl, W and Y are not both $CCH_3$;

one of R and $R^2$ (preferably $R^2$) is $NR^3R^4$ and the other is halo;

$R^1$ is aryl, heteroaryl, morpholino, piperidino or pyrrolidino;

$R^3$ and $R^4$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl($C_{1-6}$)alkyl, heteroaryl, heteroaryl($C_{1-8}$)alkyl, $NR^5R^6$, provided that not both $R^1$ and $R^4$ are H or $NR^5R^6$, or $R^3$ and $R^4$ together form a $C_{3-7}$ alkylene or 3 $C_{3-7}$ alkenylene chain optionally substituted with one or more $C_{1-4}$ alkyl or $C_{1-4}$ alkoxy groups, or, together with the nitrogen atom to which they are attached, $R^3$ and $R^4$ form a morpholine, thiomorpholine, thiomorpholine S-oxide or thiomorpholine S-dioxide ring or a piperazine or piperazine N—($C_{1-4}$)alkyl (especially N-methyl) ring; and $R^5$ and $R^6$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl($C_{1-6}$)alkyl, heteroaryl or heteroaryl($C_{1-8}$)alkyl;

any of the foregoing alkyl, alkenyl, alkynyl or cycloalkyl groups or moieties (other than for $R^8$) being optionally substituted with halogen, cyano, $C_{1-6}$ alkoxy, $C_{1-6}$ alkylcarbonyl, $C_{1-6}$ alkoxycarbonyl, $C_{1-6}$ haloalkoxy, $C_{1-6}$ alkylthio, tri($C_{1-4}$)alkylsilyl, $C_{1-6}$ alkylamino or $C_{1-6}$ dialkylamino, any of the foregoing morpholine, thiomorpholine, piperidine, piperazine and pyrrolidine rings being optionally substituted with $C_{1-4}$ alkyl (especially methyl), and any of the foregoing aryl, heteroaryl, aryloxy or heteroaryl groups being optionally substituted with one or more substituents selected from halo, hydroxy, mercapto, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, halo($C_{1-6}$)alkyl, halo($C_{1-6}$)alkoxy, $C_{1-6}$ alkylthio, halo($C_{1-6}$)alkylthio, hydroxy($C_{1-6}$)alkyl, $C_{1-4}$ alkoxy($C_{1-4}$)-alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR'''' or —N=CR'''R'''', in which R''' and R'''' are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy. Of particular interest are compounds where W, X and Y are CH and Z is N.

The invention includes a compound of the general formula (1) as defined immediately above except that: $C_7$ alkylene and $C_{3-7}$ alkenylene are excluded as chains formed by $R^3$ and $R^4$; the $C_{3-6}$ chain that $R^3$ and $R^4$ may form may only be optionally substituted with one or more methyl groups; thiomorpholine, thiomorpholine S-oxide, thiomorpholine S-dioxide and piperazine are excluded as rings that $R^3$ and $R^4$ may form; tri($C_{1-4}$)alkylsilyl is excluded as a substituent of any alkyl, alkenyl, alkynyl or cycloalkyl group or moiety, and any morpholine, piperidine or pyrrolidine ring is unsubstituted.

In another aspect the invention provides a compound of the general formula (1) wherein one of W, X, Y and Z is N and the others are $CR^8$;

$R^5$ is H, halo, $C_{1-4}$ alkyl, $C_{1-4}$ alkoxy or halo($C_{1-4}$)alkyl, provided that when X is CH, Z is N, R is NHNH$_2$, $R^1$ is phenyl and $R^2$ is Cl, W and Y are not both CCH$_3$;

one of R and $R^2$ (preferably $R^2$) is $NR^3R^4$ and the other is halo;

$R^1$ is aryl, heteroaryl, morpholino, piperidino or pyrrolidino;

$R^3$ is $C_{1-4}$ alkyl, halo($C_{1-4}$)alkyl, $C_{2-4}$ alkenyl, $C_{3-4}$ cycloalkyl, $C_{3-6}$ cycloalkyl($C_{1-4}$)alkyl or phenylamino in which the phenyl ring is optionally substituted with one, two or three substituents selected from halo, $C_{1-4}$ alkyl, halo($C_{1-4}$)alkyl, $C_{1-4}$ alkoxy and halo($C_{1-4}$)alkoxy; and $R^4$ is H, $C_{1-4}$ alkyl or amino, or $R^3$ and $R^4$ together form a $C_{4-6}$ alkylene chain optionally substituted with $C_{1-4}$ alkyl or $C_{1-4}$ alkoxy, or, together with the nitrogen atom to which they are attached, $R^3$ and $R^4$ form a morpholine, thiomorpholine, thiomorpholine S-oxide or thiomorpholine S-dioxide ring or a piperazine or piperazine N—($C_{1-4}$)alkyl (especially N-methyl) ring;

any of the foregoing alkyl, alkenyl, alkynyl or cycloalkyl groups or moieties (other than for $R^8$) being optionally substituted with halogen, cyano, $C_{1-6}$ alkoxy, $C_{1-6}$ alkylcarbonyl, $C_{1-6}$ alkoxycarbonyl, $C_{1-6}$ haloalkoxy, $C_{1-6}$ alkylthio, tri($C_{1-4}$)alkylsilyl, $C_{1-6}$ alkylamino or $C_{1-6}$ dialkylamino, any of the foregoing morpholine, thiomorpholine, piperidine, piperazine and pyrrolidine rings being optionally substituted with $C_{1-4}$ alkyl (especially methyl), and any of the foregoing aryl or heteroaryl groups or moieties being optionally substituted with one or more substituents selected from halo, hydroxy, mercapto, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, halo($C_{1-6}$)alkyl, halo($C_{1-6}$)alkoxy, $C_{1-6}$ alkylthio, halo($C_{1-6}$)alkylthio, hydroxy($C_{1-6}$)alkyl, $C_{1-4}$ alkoxy($C_{1-6}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR'''' or —N=CR'''R'''', in which R''' and R'''' are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy. Of particular interest are compounds where W, X and Y are CH and Z is N.

The invention includes a compound of the general formula (1) as defined immediately above except that: the $C_{4-6}$ chain that $R^3$ and $R^4$ may form may only be optionally substituted with methyl; thiomorpholine, thiomorpholine S-oxide, thiomorpholine S-dioxide and piperazine are excluded as rings that $R^3$ and $R^4$ may form; tri($C_{1-4}$)alkylsilyl is excluded as a substituent of any alkyl, alkenyl, alkynyl or cycloalkyl group or moiety, and any morpholine, piperidine or pyrrolidine ring is unsubstituted In yet another aspect the invention provides a compound of the general formula (1) wherein one of W, X, Y and Z is N and the others are $CR^8$;

$R^8$ is H, halo, $C_{1-4}$ alkyl, $C_{1-4}$ alkoxy or halo($C_{1-4}$)alkyl, provided that when X is CH, Z is N, R is NHNH$_2$, $R^1$ is phenyl and $R^2$ is Cl, W and Y are not both CCH$_3$;

one of R and $R^2$ is $NR^3R^4$ and the other is halo, $C_{1-8}$ alkyl, $C_{1-8}$ alkoxy, $C_{1-8}$ alkylthio, $C_{2-8}$ alkenyl, $C_{2-8}$ alkynyl or cyano;

$R^1$ is optionally substituted phenyl;

$R^3$ and $R^4$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl($C_{1-6}$)alkyl, heteroaryl, heteroaryl($C_{1-8}$)alkyl, $NR^5R^6$, provided that not both $R^3$ and $R^4$ are H or $NR^5R^6$, or $R^3$ and $R^4$ together form a $C_{3-7}$ alkylene or $C_{3-7}$ alkenylene chain optionally substituted with one or more $C_{1-4}$ alkyl or $C_{1-4}$ alkoxy groups, or, together with the nitrogen atom to which they are attached, $R^3$ and $R^4$ form a morpholine, thiomorpholine, thiomorpho line S-oxide or thiomorpholine S-dioxide ring or a piperazine or piperazine N—($C_{1-4}$)alkyl (especially N-methyl) ring; and $R^5$ and $R^6$ are independently H, $C_{1-8}$ alkyl, $C_{2-8}$ alkenyl, $C_{2-8}$ alkynyl, aryl, aryl($C_{1-8}$)alkyl, $C_{3-8}$ cycloalkyl, $C_{3-8}$ cycloalkyl($C_{1-6}$)alkyl, heteroaryl or heteroaryl($C_{1-8}$)alkyl;

any of the foregoing alkyl, alkenyl, alkynyl or cycloalkyl groups or moieties (other than for $R^8$) being optionally substituted with halogen, cyano, $C_{1-6}$ alkoxy, $C_{1-6}$ alkylcarbonyl, $C_{1-6}$ alkoxycarbonyl, $C_{1-6}$ haloalkoxy, $C_{1-6}$ alkylthio, tri($C_{1-4}$)alkylsilyl, $C_{1-6}$alkylamino or $C_{1-6}$ dialkylamino, any of the foregoing morpholine, thiomorpholine, piperidine, piperazine and pyrrolidine rings being optionally substituted with $C_{1-4}$ alkyl (especially methyl), and any of the foregoing aryl or heteroaryl groups or moieties, including the phenyl group of $R^1$, being optionally substituted with one or more substituents selected from halo, hydroxy, mercapto, $C_{1-6}$ alkyl, $C_{2-6}$ alkenyl, $C_{2-6}$ alkynyl, $C_{1-4}$ alkoxy, $C_{2-6}$ alkenyloxy, $C_{2-6}$ alkynyloxy, halo($C_{1-6}$)alkyl, halo($C_{1-6}$) alkoxy, $C_{1-6}$ alkylthio, halo($C_{1-6}$)alkylthio, hydroxy-($C_{1-6}$) alkyl, $C_{1-4}$ alkoxy($C_{1-6}$)alkyl, $C_{3-6}$ cycloalkyl, $C_{3-6}$ cycloalkyl ($C_{1-4}$)alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR'''' or —N=CR'''R'''', in which R''' and R'''' are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy. Of particular interest are compounds where W, X and Y are CH and Z is N.

The invention includes a compound of the general formula (1) as defined immediately above except that: $C_{1-8}$ alkoxy and $C_{1-8}$ alkylthio are excluded as values of R and $R^2$; $C_7$ alkylene and $C_{3-7}$ alkenylene are excluded as chains formed by $R^3$ and $R^4$; the $C_{3-6}$ chain that $R^3$ and $R^4$ may form may only be optionally substituted with one or more methyl groups; thiomorpholine, thiomorpholine S-oxide, thiomorpholine S-dioxide and piperazine are excluded as rings that $R^3$ and $R^4$ may form; tri($C_{1-4}$)alkylsilyl is excluded as a substituent of any alkyl, alkenyl, alkynyl or cycloalkyl group or moiety, and the morpholine ring that $R^3$ and $R^4$ may form is unsubstituted.

In still yet another aspect the invention provides a compound of the general formula (1) wherein
one of W, X, Y and Z is N and the others are $CR^8$;
$R^8$ is H, halo (e.g. fluoro, chloro or bromo), $C_{1-4}$ alkyl (e.g. methyl), $C_{1-4}$ alkoxy (e.g. methoxy) or halo($C_{1-4}$)alkyl (e.g. trifluoromethyl), provided that when X is CH, Z is N, R is NHNH$_2$, $R^1$ is phenyl and $R^2$ is Cl, W and Y are not both CCH$_3$;
R is halo (e.g. fluoro, chloro or bromo), $C_{1-4}$ alkyl (e.g. methyl), $C_{1-4}$ alkoxy (e.g. methoxy) or cyano;
$R^1$ is phenyl optionally substituted with from one to five halogen atoms or with from one to three substituents selected from halo, $C_{1-4}$ alkyl, halo($C_{1-4}$)alkyl, $C_{1-4}$ alkoxy or halo($C_{1-4}$)-alkoxy, pyridyl optionally substituted with from one to four halogen atoms or with from one to three substituents selected from halo, $C_{1-4}$ alkyl, halo($C_{1-4}$)alkyl, $C_{1-4}$ alkoxy or halo($Cl_4$)-alkoxy, 2- or 3-thienyl optionally substituted with from one to three halogen atoms or with from one to three substituents selected from halo, $C_{1-4}$ alkyl, halo($C_{1-4}$)alkyl, $C_{1-4}$ alkoxy or halo($C_{1-4}$)alkoxy, or piperidino or morpholino both optionally substituted with one or two methyl groups;
$R^2$ is $NR^3R^4$;
$R^3$ is $C_{1-8}$ alkyl, halo($C_{1-8}$)alkyl, hydroxy($C_{1-8}$)alkyl, $C_{1-4}$ alkoxy($C_{1-8}$)alkyl, $C_{1-4}$ alkoxyhalo-($C_{1-8}$)alkyl, tri($C_{1-4}$) alkylsilyl($C_{1-6}$)alkyl, $C_{1-4}$ alkylcarbonyl($C_{1-8}$)alkyl, $C_{1-4}$ alkylcarbonyl-halo($C_{1-8}$)alkyl, phenyl($_{1-4}$)alkyl, $C_{2-8}$ alkenyl, halo($C_{2-8}$)alkenyl, $C_{2-8}$ alkynyl, $C_{3-8}$ cycloalkyl optionally substituted with chloro, fluoro or methyl, $C_{3-8}$ cycloalkyl ($C_{1-4}$)alkyl, phenylamino, piperidino or morpholino, the phenyl ring of phenylalkyl or phenylamino being optionally substituted with one, two or three substituents selected from halo, $C_{1-4}$ alkyl, halo($C_{1-4}$)alkyl, $C_{1-4}$ alkoxy and halo($C_{1-4}$) alkoxy; and
$R^4$ is H, $C_{1-4}$ alkyl, halo($C_{1-4}$)alkyl or amino, or $R^3$ and $R^4$ together form a $C_{3-7}$ alkylene or $C_{3-7}$ alkenylene chain optionally substituted with methyl, or,
together with the nitrogen atom to which they are attached, $R^3$ and $R^4$ form a morpholine, thiomorpholine, thiomorpholine S-oxide or thiomorpholine S-dioxide ring or a piperazine or piperazine N—($C_{1-4}$)alkyl (especially N-methyl) ring, in which the morpholine or piperazine rings are optionally substituted with methyl. Of particular interest are compounds where W, X and Y are CH and Z is N.

In still yet another aspect the invention provides a compound of the general formula (1) wherein
one of W, X, Y and Z is N and the others are $CR^8$;
$R^8$ is H, halo, $C_{1-4}$ alkyl, $C_{1-4}$ alkoxy or halo($C_{1-4}$)alkyl;
R is halo;
$R^1$ is phenyl optionally substituted with from one to five halogen atoms or with from one to three substituents selected from halo, $C_{1-4}$ alkyl, halo($C_{1-4}$)alkyl, $C_{1-4}$ alkoxy or halo($C_{1-4}$)-alkoxy;
$R^2$ is $NR^3R^4$;
$R^3$ is $C_{1-4}$ alkyl, halo($C_{1-4}$)alkyl, $C_{2-4}$ alkenyl, $C_{3-6}$ cycloalkyl, $C_{3-6}$ cycloalkyl($C_{1-4}$)alkyl or phenylamino in which the phenyl ring is optionally substituted with one, two or three substituents selected from halo, $C_{1-4}$ alkyl, halo($C_{1-4}$)alkyl, $C_{1-4}$ alkoxy and halo($C_{1-4}$)alkoxy; and
$R^4$ is H, $C_{1-4}$ alkyl or amino, or $R^3$ and $R^4$ together form a $C_{4-6}$ alkylene chain optionally substituted with methyl, or, together with the nitrogen atom to which they are attached, $R^3$ and $R^4$ form a morpholine ring.
Of particular interest are compounds where W, X and Y are CH and Z is N.

Compounds that form part of the invention are illustrated in Tables 1 to 126 below. Characterising data are given later in the Examples and in Table 132

In Table 1 the compounds have the general formula (1A), where W, X and Y are CH, Z is N, R is Cl, $R^1$ is 2,4,6-trifluorophenyl and $R^3$ and $R^4$ are as shown in the table.

TABLE 1

(1A)

| Cmpd No | $R^3$ | $R^4$ |
|---|---|---|
| 1 | $C_2H_5$ | H |
| 2 | n-$C_3H_7$ | H |
| 3 | i-$C_3H_7$ | H |
| 4 | n-$C_4H_9$ | H |
| 5 | t-$C_4H_9$ | H |
| 6 | $CH_2$=CHCH$_2$ | H |
| 7 | $CH_2$=C(CH$_3$)CH$_2$ | H |
| 8 | $CF_3CH_2$ | H |
| 9 | $CF_3CH_2CH_2$ | H |
| 10 | $CF_3CH_2CH_2CH_2$ | H |
| 11 | $CF_3(CH_3)CH$ | H |
| 12 | (S)-$CF_3(CH_3)CH$ | H |
| 13 | (R)-$CF_3(CH_3)CH$ | H |
| 14 | cyclo-$C_3H_5$ | H |
| 15 | cyclo-$C_4H_7$ | H |
| 16 | cyclo-$C_5H_9$ | H |
| 17 | cyclo-$C_6H_{11}$ | H |
| 18 | cyclo-$C_3H_5CH_2$ | H |
| 19 | cyclo-$C_4H_7CH_2$ | H |
| 20 | —(CH$_2$)$_2$O(CH$_2$)$_2$— | |
| 21 | cyclo-$C_6H_{11}CH_2$ | H |

TABLE 1-continued (1A)

| Cmpd No | R³ | R⁴ |
|---|---|---|
| 22 | —(CH₂)₂CH(CH₃)(CH₂)₂— | |
| 23 | CH₃CH₂(CH₃)CH | H |
| 24 | (S)-CH₃CH₂(CH₃)CH | H |
| 25 | (R)-CH₃CH₂(CH₃)CH | H |
| 26 | C₂H₅ | C₂H₅ |
| 27 | n-C₃H₇ | n-C₃H₇ |
| 28 | CH₂=C(CH₃)CH₂ | C₂H₅ |
| 29 | CF₃CH₂ | C₂H₅ |
| 30 | C₂H₅ | NH₂ |
| 31 | n-C₃H₇ | NH₂ |
| 32 | i-C₃H₇ | NH₂ |
| 33 | n-C₄H₉ | NH₂ |
| 34 | CH₂=CHCH₂ | NH₂ |
| 35 | CH₂=C(CH₃)CH₂ | NH₂ |
| 36 | CF₂=CFCH₂CH₂ | NH₂ |
| 37 | CF₃CH₂ | NH₂ |
| 38 | CF₃CH₂CH₂ | NH₂ |
| 39 | CF₃CF₂CH₂CH₂ | NH₂ |
| 40 | 4-t-C₄H₉—C₆H₄NH | H |
| 41 | 4-F—C₆H₄NH | H |
| 42 | C₆H₅NH | H |
| 43 | 4-CH₃—C₆H₄NH | H |
| 44 | 4-Br—C₆H₄NH | H |
| 45 | 2-F—C₆H₄NH | H |
| 46 | 3,4-Cl₂—C₆H₃NH | H |
| 47 | 3-CF₃—C₆H₄NH | H |
| 48 | 3,5-Cl₂—C₆H₃NH | H |
| 49 | 4-CF₃O—C₆H₅NH | H |
| 50 | 2-CF₃—C₆H₄NH | H |
| 51 | 4-CF₃—C₆H₄NH | H |
| 52 | 2-Br—C₆H₄NH | H |
| 53 | 2-Cl—C₆H₄NH | H |
| 54 | 2-CH₃-4-Cl—C₆H₃NH | H |
| 55 | 2-CH₃-5-F—C₆H₃NH | H |
| 56 | 3-Cl—C₆H₄NH | H |
| 57 | CH₃ | H |
| 58 | (CH₃)₂CHCH₂ | H |
| 59 | (CH₃)₃CCH₂ | H |
| 60 | (CH₃)₃C(CH₃)CH | H |
| 61 | CH₃CH₂(CH₃)₂C | H |
| 62 | CH₃CH₂(CF₃)CH | H |
| 63 | (S)-CH₃CH₂(CF₃)CH | H |
| 64 | (R)-CH₃CH₂(CF₃)CH | H |
| 65 | CH₃CH₂(CH₃CH₂)CH | H |
| 66 | (CH₃)₂CH(CH₃CH₂)CH | H |
| 67 | (CH₃)₂CH(CH₃)CH | H |
| 68 | (CH₃)₂CH(CF₃)CH | H |
| 69 | (S)-(CH₃)₂CH(CF₃)CH | H |
| 70 | (R)-(CH₃)₂CH(CF₃)CH | H |
| 71 | HC≡C(CH₃)₂CH₂ | H |
| 72 | CH₂=CH(CH₃CH₂)CH | H |
| 73 | CH₃CH₂CH₂(CH₃)CH | H |
| 74 | CH₃CH₂CH₂(CF₃)CH | H |
| 75 | (S)-CH₃CH₂CH₂(CF₃)CH | H |
| 76 | (R)-CH₃CH₂CH₂(CF₃)CH | H |
| 77 | CH₃CH₂(CH₃)₂C | H |
| 78 | CH₃CH₂(CH₃)CHCH₂ | H |
| 79 | (CH₃)₂CHCH₂CH₂ | H |
| 80 | (CH₃)₃CCH₂CH₂ | H |
| 81 | CH₃CH₂(CH₃)CH(CH₃)—CH | H |
| 82 | CH₃CH₂(CH₃)CH(CF₃)—CH | H |
| 83 | (S)-CH₃CH₂(CH₃)CH—(CF₃)CH | H |
| 84 | (R)-CH₃CH₂(CH₃)CH—(CF₃)CH | H |
| 85 | CH₃(CH₃)CHCH₂(CH₃)—CH | H |
| 86 | CH₃(CH₃)CHCH₂(CF₃)—CH | H |
| 87 | (S)-CH₃(CH₃)CHCH₂—(CF₃)CH | H |
| 88 | (R)-CH₃(CH₃)CHCH₂—(CF₃)CH | H |
| 89 | (CH₃)₂CH(CH₃)CH—(CH₃)CH₂ | H |
| 90 | (CH₃)₃CCH₂(CH₃)CH | H |
| 91 | E-CH₃CH=CH(CH₃)CH | H |
| 92 | E-CH₃CH=CH(CH₃CH₂)—CH | H |
| 93 | CH₃CH₂CH₂(CH₃CH₂)—CH | H |
| 94 | CH₃CH₂(CH₃CH₂)—CHCH₂ | H |
| 95 | CF₂=CFCH₂CH₂ | H |
| 96 | CF₃CH₂(CH₃)CHCH₂ | H |
| 97 | CF₃CF₂CH₂CH₂ | H |
| 98 | CF₃CF₂CF₂CH₂ | H |
| 99 | CF₂=C(CH₃)CH₂CH₂ | H |
| 100 | CH₃CH₂CH₂CH₂CH₂ | H |
| 101 | CH₃CH₂CH₂CH₂—(CH₃)CH | H |
| 102 | CH₃CH₂CH₂(CH₃)—CHCH₂ | H |
| 103 | CH₃CH₂(CH₃)CHCH₂—CH₂ | H |
| 104 | CH₃CH₂CH₂(CH₃)CH—(CH₃)CH | H |
| 105 | CH₃CH₂(CH₃)CHCH₂—(CH₃)CH | H |
| 106 | HOCH₂CH₂ | H |
| 107 | CH₃OCH₂CH₂ | H |
| 108 | CH₃OCH₂(CH₃)CH | H |
| 109 | CH₃OCH₂(CF₃)CH | H |
| 110 | CH₃OCH(CH₃)₂C | H |
| 111 | CH₃O(CH₃)CHCH₂ | H |
| 112 | CH₃O(CH₃)CH(CH₃)CH | H |
| 113 | HC≡CCH₂ | H |
| 114 | CH₃C≡CCH₂ | H |
| 115 | HC≡CCH₂CH₂ | H |
| 116 | HOCH₂CH₂CH₂ | H |
| 117 | CH₃OCH₂CH₂CH₂ | H |
| 118 | (CH₃)₃SiCH₂ | H |
| 119 | C₆H₅CH₂ | H |
| 120 | C₆H₅(CH₃)CH | H |
| 121 | 4-F—C₆H₄CH₂ | H |
| 122 | 4-Cl—C₆H₄CH₂ | H |
| 123 | 4-F—C₆H₅(CH₃)CH | H |
| 124 | 4-Cl—C₆H₅(CH₃)CH | H |
| 125 | C₆H₅CH₂CH₂ | H |
| 126 | 4-F—C₆H₅CH₂CH₂ | H |
| 127 | 1-piperidino | H |
| 128 | 1-pyrrolidino | H |
| 129 | cyclo-C₆H₉CH₂ | H |
| 130 | Bicyclo[2.2.1]hept-2-yl | H |
| 131 | 1-CH₃-cyclopropyl | H |
| 132 | cis-2-CH₃-cyclopropyl | H |
| 133 | trans-2-CH₃-cyclopropyl | H |
| 134 | 2,2-(CH₃)₂-cyclopropyl | H |
| 135 | 1-CH₃-cyclobutyl | H |
| 136 | cis-2-CH₃-cyclobutyl | H |
| 137 | trans-2-CH₃-cyclobutyl | H |
| 138 | cis-3-CH₃-cyclobutyl | H |
| 139 | trans-3-CH₃-cyclobutyl | H |
| 140 | 2,2-(CH₃)₂-cyclobutyl | H |
| 141 | 3,3-(CH₃)₂-cyclobutyl | H |
| 142 | 1-CH₃-cyclopentyl | H |
| 143 | cis-2-CH₃-cyclopentyl | H |
| 144 | trans-2-CH₃-cyclopentyl | H |
| 145 | cis-3-CH₃-cyclopentyl | H |
| 146 | trans-3-CH₃-cyclopentyl | H |
| 147 | 2,2-(CH₃)₂-cyclopentyl | H |
| 148 | 3,3-(CH₃)₂-cyclopentyl | H |
| 149 | 1-CH₃-cyclohexyl | H |
| 150 | cis-2-CH₃-cyclohexyl | H |
| 151 | trans-2-CH₃-cyclohexyl | H |
| 152 | cis-3-CH₃-cyclohexyl | H |
| 153 | trans-3-CH₃-cyclohexyl | H |
| 154 | 2,2-(CH₃)₂-cyclohexyl | H |
| 155 | 3,3-(CH₃)₂-cyclohexyl | H |

TABLE 1-continued (1A)

| Cmpd No | R³ | R⁴ |
|---|---|---|
| 156 | cis-4-CH₃-cyclohexyl | H |
| 157 | trans-4-CH₃-cyclohexyl | H |
| 158 | 4,4-(CH₃)₂-cyclohexyl | H |
| 159 | 4-(CH₃)₃C-cyclohexyl | H |
| 160 | —(CH₂)₃— | |
| 161 | —(CH₂)₄— | |
| 162 | —(CH₂)₅— | |
| 163 | —(CH₂)₆— | |
| 164 | —(CH₂)₂(CH₃)₂C(CH₂)₂— | |
| 165 | —(CH₃)CH(CH₂)₂— | |
| 166 | —(CH₃)CH(CH₂)₃— | |
| 167 | —(CH₃)CH(CH₂)₄— | |
| 168 | —(CH₃)CH(CH₂)₅— | |
| 169 | —CH₂CH═CH(CH₂)₂— | |
| 170 | —(CH₂)₂NH(CH₂)₂— | |
| 171 | —(CH₂)₂NCH₃(CH₂)₂— | |
| 172 | —(CH₂)₂S(CH₂)₂— | |
| 173 | —(CH₂)₂SO(CH₂)₂— | |
| 174 | —(CH₂)₂SO₂(CH₂)₂— | |
| 175 | —CH₂(CH₃)CHO(CH₃)CHCH₂— | |
| 176 | C₂H₅ | CH₃ |
| 177 | n-C₃H₇ | CH₃ |
| 178 | i-C₃H₇ | CH₃ |
| 179 | n-C₄H₉ | CH₃ |
| 180 | t-C₄H₉ | CH₃ |
| 181 | CH₂═CHCH₂ | CH₃ |
| 182 | CH₂═C(CH₃)CH₂ | CH₃ |
| 183 | CF₃CH₂ | CH₃ |
| 184 | CF₃CH₂CH₂ | CH₃ |
| 185 | CF₃CH₂CH₂CH₂ | CH₃ |
| 186 | CF₃(CH₃)CH | CH₃ |
| 187 | (S)-CF₃(CH₃)CH | CH₃ |
| 188 | (R)-CF₃(CH₃)CH | CH₃ |
| 189 | cyclo-C₃H₅ | CH₃ |
| 190 | cyclo-C₄H₇ | CH₃ |
| 191 | cyclo-C₅H₉ | CH₃ |
| 192 | cyclo-C₆H₁₁ | CH₃ |
| 193 | cyclo-C₃H₅CH₂ | CH₃ |
| 194 | cyclo-C₄H₇CH₂ | CH₃ |
| 195 | cyclo-C₆H₁₁CH₂ | CH₃ |
| 196 | CH₃CH₂(CH₃)CH | CH₃ |
| 197 | (S)-CH₃CH₂(CH₃)CH | CH₃ |
| 198 | (R)-CH₃CH₂(CH₃)CH | CH₃ |
| 199 | cyclo-C₇H₁₃ | CH₃ |
| 200 | CH₂═C(CH₃)CH₂ | CH₃ |
| 201 | CF₃CH₂ | CH₃ |
| 202 | 4-t-C₄H₉—C₆H₄NH | CH₃ |
| 203 | 4-F—C₆H₄NH | CH₃ |
| 204 | C₆H₅NH | CH₃ |
| 205 | 4-CH₃—C₆H₄NH | CH₃ |
| 206 | 4-Br—C₆H₄NH | CH₃ |
| 207 | 2-F—C₆H₄NH | CH₃ |
| 208 | 3,4-Cl₂—C₆H₃NH | CH₃ |
| 209 | 3-CF₃—C₆H₄NH | CH₃ |
| 210 | 3,5-Cl₂—C₆H₃NH | CH₃ |
| 211 | 4-CF₃O—C₆H₅NH | CH₃ |
| 212 | 2-CF₃—C₆H₄NH | CH₃ |
| 213 | 4-CF₃—C₆H₄NH | CH₃ |
| 214 | 2-Br—C₆H₄NH | CH₃ |
| 215 | 2-Cl—C₆H₄NH | CH₃ |
| 216 | 2-CH₃-4-Cl—C₆H₃NH | CH₃ |
| 217 | 2-CH₃-5-F—C₆H₃NH | CH₃ |
| 218 | 3-Cl—C₆H₄NH | CH₃ |
| 219 | CH₃ | CH₃ |
| 220 | (CH₃)₂CHCH₂ | CH₃ |
| 221 | (CH₃)₃CCH₂ | CH₃ |
| 222 | (CH₃)₃C(CH₃)CH | CH₃ |
| 223 | CH₃CH₂(CH₃)₂C | CH₃ |
| 224 | CH₃CH₂(CF₃)CH | CH₃ |
| 225 | (S)-CH₃CH₂(CF₃)CH | CH₃ |
| 226 | (R)-CH₃CH₂(CF₃)CH | CH₃ |
| 227 | CH₃CH₂(CH₃CH₂)CH | CH₃ |
| 228 | (CH₃)₂CH(CH₃CH₂)CH | CH₃ |
| 229 | (CH₃)₂CH(CH₃)CH | CH₃ |
| 230 | (CH₃)₂CH(CF₃)CH | CH₃ |
| 231 | (S)-(CH₃)₂CH(CF₃)CH | CH₃ |
| 232 | (R)-(CH₃)₂CH(CF₃)CH | CH₃ |
| 233 | HC═C(CH₃)CH₂ | CH₃ |
| 234 | CH₂═CH(CH₃CH₂)CH | CH₃ |
| 235 | CH₃CH₂CH₂(CH₃)CH | CH₃ |
| 236 | CH₃CH₂CH₂(CF₃)CH | CH₃ |
| 237 | (S)-CH₃CH₂CH₂(CF₃)CH | CH₃ |
| 238 | (R)-CH₃CH₂CH₂(CF₃)CH | CH₃ |
| 239 | CH₃CH₂CH₂(CH₃)₂C | CH₃ |
| 240 | CH₃CH₂(CH₃)CHCH₂ | CH₃ |
| 241 | (CH₃)₂CHCH₂CH₂ | CH₃ |
| 242 | (CH₃)₃CCH₂CH₂ | CH₃ |
| 243 | CH₃CH₂(CH₃)CH(CH₃)—CH | CH₃ |
| 244 | CH₃CH₂(CH₃)CH(CF₃)—CH | CH₃ |
| 245 | (S)-CH₃CH₂(CH₃)CH—(CF₃)CH | CH₃ |
| 246 | (R)-CH₃CH₂(CH₃)CH—(CF₃)CH | CH₃ |
| 247 | CH₃(CH₃)CHCH₂—(CH₃)CH | CH₃ |
| 248 | CH₃(CH₃)CHCH₂—(CF₃)CH | CH₃ |
| 249 | (S)-CH₃(CH₃)CHCH₂—(CF₃)CH | CH₃ |
| 250 | (R)-CH₃(CH₃)HCH₂—(CF₃)CH | CH₃ |
| 251 | (CH₃)₂CH(CH₃)CH(CH₃)—CH₂ | CH₃ |
| 252 | (CH₃)₃CCH—(CH₃)CH | CH₃ |
| 253 | E-CH₃CH═CH(CH₃)CH | CH₃ |
| 254 | E-CH₃CH═CH(CH₃CH₂)—CH | CH₃ |
| 255 | CH₃CH₂(CH₃CH₂)—CH | CH₃ |
| 256 | CH₃CH₂(CH₃CH₂)—CHCH₂ | CH₃ |
| 257 | CF₂═CFCH₂ | CH₃ |
| 258 | CF₃CH₂(CH₃)CHCH₂ | CH₃ |
| 259 | CF₃CF₂CH₂CH₂ | CH₃ |
| 260 | CF₃CF₂CF₂CH₂ | CH₃ |
| 261 | CF₂═C(CH₃)CH₂CH₂ | CH₃ |
| 262 | CH₃CH₂CH₂CH₂CH₂ | CH₃ |
| 263 | CH₃CH₂CH₂CH₂(CH₃)—CH | CH₃ |
| 264 | CH₃CH₂CH₂(CH₃)—CHCH₂ | CH₃ |
| 265 | CH₃CH₂CH₂(CH₃)CH—CH₂ | CH₃ |
| 266 | CH₃CH₂CH₂(CH₃)CH—(CH₃)CH | CH₃ |
| 267 | CH₃CH₂(CH₃)CHCH₂—(CH₃)CH | CH₃ |
| 268 | HOCH₂CH₂ | CH₃ |
| 269 | CH₃OCH₂CH₂ | CH₃ |
| 270 | CH₃OCH₂(CH₃)CH | CH₃ |
| 271 | CH₃OCH₂(CF₃)CH | CH₃ |
| 272 | CH₃OCH₂(CH₃)₂C | CH₃ |
| 273 | CH₃O(CH₃)CHCH₂ | CH₂ |
| 274 | CH₃O(CH₃)CH(CH₃)CH | CH₃ |
| 275 | HC═CH₂ | CH₃ |
| 276 | CH₃C═CCH₂ | CH₃ |
| 277 | HC═CCH₂CH₂ | CH₃ |
| 278 | HOCH₂CH₂ | CH₃ |
| 279 | CH₃OCH₂CH₂CH₂ | CH₃ |
| 280 | (CH₃)₃SiCH₂ | CH₃ |
| 281 | C₆H₅CH₂ | CH₃ |
| 282 | C₆H₅(CH₃)CH | CH₃ |
| 283 | 4-F—C₆H₄₂ | H |
| 284 | 4-Cl—C₆H₄₂ | CH₃ |
| 285 | 4-F—C₆H₅(CH₃)CH | CH₃ |
| 286 | 4-Cl—C₆H₅(CH₃)CH | CH₃ |
| 287 | C₆H₅CH₂CH₂ | CH₃ |
| 288 | 4-F—C₆H₅CH₂CH₂ | CH₃ |
| 289 | 1-piperidino | CH₃ |

TABLE 1-continued (1A)

| Cmpd No | R³ | R⁴ |
|---|---|---|
| 290 | 1-pyrrolidino | CH₃ |
| 291 | cyclo-C₅H₉CH₂ | CH₃ |
| 292 | bicyclo[2.2.1]hept-2-yl | CH₃ |
| 293 | 1-CH₃-cyclopropyl | CH₃ |
| 294 | cis-2-CH₃-cyclopropyl | CH₃ |
| 295 | trans-2-CH₃-cyclopropyl | CH₃ |
| 296 | 2,2-(CH₃)₂-cyclopropyl | CH₃ |
| 297 | 1-CH₃-cyclobutyl | CH₃ |
| 298 | cis-2-CH₃-cyclobutyl | CH₃ |
| 299 | trans-2-CH₃-cyclobutyl | CH₃ |
| 300 | cis-3-CH₃-cyclobutyl | CH₃ |
| 301 | trans-3-CH₃-cyclobutyl | CH₃ |
| 302 | 2,2-(CH₃)₂-cyclobutyl | CH₃ |
| 303 | 3,3-(CH₃)₂-cyclobutyl | CH₃ |
| 304 | 1-CH₃-cyclopentyl | CH₃ |
| 305 | cis-2-CH₃-cyclopentyl | CH₃ |
| 306 | trans-2-CH₃-cyclopentyl | CH₃ |
| 307 | cis-3-CH₃-cyclopentyl | CH₃ |
| 308 | trans-3-CH₃-cyclopentyl | CH₃ |
| 309 | 2,2-(CH₃)₂-cyclopentyl | CH₃ |
| 310 | 3,3-(CH₃)₂-cyclopentyl | CH₃ |
| 311 | 1-CH₃-cyclohexyl | CH₃ |
| 312 | cis-2-CH₃-cyclohexyl | CH₃ |
| 313 | trans-2-CH₃-cyclohexyl | CH₃ |
| 314 | cis-3-CH₃-cyclohexyl | CH₃ |
| 315 | trans-3-CH₃-cyclohexyl | CH₃ |
| 316 | 2,2-(CH₃)₂-cyclohexyl | CH₃ |
| 317 | 3,3-(CH₃)₂-cyclohexyl | CH₃ |
| 318 | cis-4-CH₃-cyclohexyl | CH₃ |
| 319 | trans-4-CH₃-cyclohexyl | CH₃ |
| 320 | 4,4-(CH₃)₂-cyclohexyl | CH₃ |
| 321 | 4-(CH₃)₃C-cyclohexyl | CH₃ |
| 322 | n-C₃H₇ | C₂H₅ |
| 323 | i-C₃H₇ | C₂H₅ |
| 324 | n-C₄H₉ | C₂H₅ |
| 325 | t-C₄H₉ | C₂H₅ |
| 326 | CH₂=CHCH₂ | C₂H₅ |
| 327 | CF₃CH₂CH₂ | C₂H₅ |
| 328 | CF₃CH₂CH₂ | C₂H₅ |
| 329 | CF₃(CH₃)CH | C₂H₅ |
| 330 | (S)-CF₃(CH₃)CH | C₂H₅ |
| 331 | (R)-CF₃(CH₃)CH | C₂H₅ |
| 332 | cyclo-C₃H₅ | C₂H₅ |
| 333 | cyclo-C₄H₇ | C₂H₅ |
| 334 | cyclo-C₅H₉ | C₂H₅ |
| 335 | cyclo-C₆H₁₁ | C₂H₅ |
| 336 | cyclo-C₃H₅CH₂ | C₂H₅ |
| 337 | cyclo-C₄H₇CH₂ | C₂H₅ |
| 338 | cyclo-C₆H₁₁CH₂ | C₂H₅ |
| 339 | CH₃CH₂(CH₃)CH | C₂H₅ |
| 340 | (S)-CH₃CH₂(CH₃)CH | C₂H₅ |
| 341 | (R)-CH₃CH₂(CH₃)CH | C₂H₅ |
| 342 | cyclo-C₇H₁₃ | C₂H₅ |
| 343 | 4-t-C₄H₉—C₆H₄NH | C₂H₅ |
| 344 | 4-F—C₆H₄NH | C₂H₅ |
| 345 | C₆H₅NH | C₂H₅ |
| 346 | 4-CH₃—C₆H₄NH | C₂H₅ |
| 347 | 4-Br—C₆H₄NH | C₂H₅ |
| 348 | 2-F—C₆H₄NH | C₂H₅ |
| 349 | 3,4-Cl₂—C₆H₃NH | C₂H₅ |
| 350 | 3-CF₃—C₆H₄NH | C₂H₅ |
| 351 | 3,5-Cl₂—C₆H₃NH | C₂H₅ |
| 352 | 4-CF₃O—C₆H₅NH | C₂H₅ |
| 353 | 2-CF₃—C₆H₄NH | C₂H₅ |
| 354 | 4-CF₃—C₆H₄NH | C₂H₅ |
| 355 | 2-Br—C₆H₄NH | C₂H₅ |
| 356 | 2-Cl—C₆H₄NH | C₂H₅ |
| 357 | 2-CH₃-4-Cl—C₆H₃NH | C₂H₅ |
| 358 | 2-CH₃-5-F—C₆H₃NH | C₂H₅ |
| 359 | 3-Cl—C₆H₄NH | C₂H₅ |
| 360 | (CH₃)₂CHCH₂ | C₂H₅ |
| 361 | (CH₃)₃CCH₂ | C₂H₅ |
| 362 | (CH₃)₃C(CH₃)CH | C₂H₅ |
| 363 | CH₃CH₂(CH₃)₂C | C₂H₅ |
| 364 | CH₃CH₂(CF₃)CH | C₂H₅ |
| 365 | (S)-CH₃CH₂(CF₃)CH | C₂H₅ |
| 366 | (R)-CH₃CH₂(CF₃)CH | C₂H₅ |
| 367 | CH₃CH₂(CH₃CH₂)CH | C₂H₅ |
| 368 | (CH₃)₂CH(CH₃CH₂)CH | C₂H₅ |
| 369 | (CH₃)₂CH(CH₃)CH | C₂H₅ |
| 370 | (CH₃)₂CH(CF₃)CH | C₂H₅ |
| 371 | (S)-(CH₃)₂CH(CF₃)CH | C₂H₅ |
| 372 | (R)-(CH₃)₂CH(CF₃)CH | C₂H₅ |
| 373 | HC≡C(CH₃)CH₂ | C₂H₅ |
| 374 | CH₂=CH(CH₃CH₂)CH | C₂H₅ |
| 375 | CH₃CH₂CH₂(CH₃)CH | C₂H₅ |
| 376 | CH₃CH₂CH₂(CF₃)CH | C₂H₅ |
| 377 | (S)-CH₃CH₂CH₂(CF₃)CH | C₂H₅ |
| 378 | (R)-CH₃CH₂CH₂(CF₃)CH | C₂H₅ |
| 379 | CH₃CH₂CH₂(CH₃)₂C | C₂H₅ |
| 380 | CH₃CH₂(CH₃)CHCH₂ | C₂H₅ |
| 381 | (CH₃)₂CHCH₂CH₂ | C₂H₅ |
| 382 | (CH₃)₃CCH₂CH₂ | C₂H₅ |
| 383 | CH₃CH₂(CH₃)CH(CH₃)—CH | C₂H₅ |
| 384 | CH₃CH₂(CH₃)CH(CF₃)—CH | C₂H₅ |
| 385 | (S)-CH₃CH₂(CH₃)CH—(CF₃)CH | C₂H₅ |
| 386 | (R)-CH₃CH₂(CH₃)CH—(CF₃)CH | C₂H₅ |
| 387 | CH₃(CH₃)CHCH₂(CH₃)—CH | C₂H₅ |
| 388 | CH₃(CH₃)CHCH₂(CF₃)—CH | C₂H₅ |
| 389 | (S)-CH₃(CH₃)CHCH₂—(CF₃)CH | C₂H₅ |
| 390 | (R)-CH₃(CH₃)CHCH₂—(CF₃)CH | C₂H₅ |
| 391 | (CH₃)₂CH(CH₃)CH—(CH₃)CH₂ | C₂H₅ |
| 392 | (CH₃)₃CCH₂(CH₃)CH | C₂H₅ |
| 393 | E-CH₃CH=CH(CH₃)CH | C₂H₅ |
| 394 | E-CH₃CH=CH—(CH₃CH₂)CH | C₂H₅ |
| 395 | CH₃CH₂CH₂(CH₃₂)—CH | C₂H₅ |
| 396 | CH₃CH₂(CH₃CH₂)CH—CH₂ | C₂H₅ |
| 397 | CF₂=CFCH₂CH₂ | C₂H₅ |
| 398 | CF₃CH₂(CH₃)CHCH₂ | C₂H₅ |
| 399 | CF₃CF₂CH₂CH₂ | C₂H₅ |
| 400 | CF₃CF₂CF₂CH₂ | C₂H₅ |
| 401 | CF₂=C(CH₃)CH₂CH₂ | C₂H₅ |
| 402 | CH₃CH₂CH₂CH₂CH₂ | C₂H₅ |
| 403 | CH₃CH₂CH₂(CH₃)—CH | C₂H₅ |
| 404 | CH₃CH₂(CH₃)CH—CH₂ | C₂H₅ |
| 405 | CH₃CH₂(CH₃)CHCH₂—CH₂ | C₂H₅ |
| 406 | CH₃CH₂CH₂(CH₃)CH—(CH₃)CH | C₂H₅ |
| 407 | CH₃CH₂(CH₃)CHCH₂—(CH₃)CH | C₂H₅ |
| 408 | HOCH₂ | C₂H₅ |
| 409 | CH₃OCH₂CH₂ | C₂H₅ |
| 410 | CH₃OCH₂(CH₃)CH | C₂H₅ |
| 411 | CH₃OCH₂(CF₃)CH | C₂H₅ |
| 412 | CH₃OCH₂(CH₃)₂C | C₂H₅ |
| 413 | CH₃O(CH₃)CHCH₂ | C₂H₅ |
| 414 | CH₃O(CH₃)CH(CH₃)CH | C₂H₅ |
| 415 | HC≡CH₂ | C₂H₅ |
| 416 | CH₃C≡CCH₂ | C₂H₅ |
| 417 | HC≡CCH₂CH₂ | C₂H₅ |
| 418 | HOCH₂CH₂CH₂ | C₂H₅ |
| 419 | CH₃OCH₂CH₂CH₂ | C₂H₅ |
| 420 | (CH₃)₃SiCH₂ | C₂H₅ |
| 421 | C₆H₅CH₂ | C₂H₅ |
| 422 | C₆H₅(CH₃)CH | C₂H₅ |
| 423 | 4-F—C₆H₄CH₂ | C₂H₅ |

TABLE 1-continued (1A)

| Cmpd No | R³ | R⁴ |
|---|---|---|
| 424 | 4-Cl—C₆H₄CH₂ | C₂H₅ |
| 425 | 4-F—C₆H₅(CH₃)CH | C₂H₅ |
| 426 | 4-Cl—C₆H₅(CH₃)CH | C₂H₅ |
| 427 | C₆H₅CH₂CH₂ | C₂H₅ |
| 428 | 4-F—C₆H₅CH₂CH₂ | C₂H₅ |
| 429 | 1-piperidino | C₂H₅ |
| 430 | 1-pyrrolidino | C₂H₅ |
| 431 | cyclo-C₅H₉CH₂ | C₂H₅ |
| 432 | Bicyclo[2.2.1]hept-2-yl | C₂H₅ |
| 433 | 1-CH₃-cyclopropyl | C₂H₅ |
| 434 | cis-2-CH₃-cyclopropyl | C₂H₅ |
| 435 | trans-2-CH₃-cyclopropyl | C₂H₅ |
| 436 | 2,2-(CH₃)₂-cyclopropyl | C₂H₅ |
| 437 | 1-CH₃-cyclobutyl | C₂H₅ |
| 438 | cis-2-CH₃-cyclobutyl | C₂H₅ |
| 439 | trans-2-CH₃-cyclobutyl | C₂H₅ |
| 440 | cis-3-CH₃-cyclobutyl | C₂H₅ |
| 441 | trans-3-CH₃-cyclobutyl | C₂H₅ |
| 442 | 2,2-(CH₃)₂-cyclobutyl | C₂H₅ |
| 443 | 3,3-(CH₃)₂-cyclobutyl | C₂H₅ |
| 444 | 1-CH₃-cyclopentyl | C₂H₅ |
| 445 | cis-2-CH₃-cyclopentyl | C₂H₅ |
| 446 | trans-2-CH₃-cyclopentyl | C₂H₅ |
| 447 | cis-3-CH₃-cyclopentyl | C₂H₅ |
| 448 | trans-3-CH₃-cyclopentyl | C₂H₅ |
| 449 | 2,2-(CH₃)₂-cyclopentyl | C₂H₅ |
| 450 | 3,3-(CH₃)₂-cyclopentyl | C₂H₅ |
| 451 | 1-CH₃-cyclohexyl | C₂H₅ |
| 452 | cis-2-CH₃-cyclohexyl | C₂H₅ |
| 453 | trans-2-CH₃-cyclohexyl | C₂H₅ |
| 454 | cis-3-CH₃-cyclohexyl | C₂H₅ |
| 455 | trans-3-CH₃-cyclohexyl | C₂H₅ |
| 456 | 2,2-(CH₃)₂-cyclohexyl | C₂H₅ |
| 457 | 3,3-(CH₃)₂-cyclohexyl | C₂H₅ |
| 458 | cis-4-CH₃-cyclohexyl | C₂H₅ |
| 459 | trans-4-CH₃-cyclohexyl | C₂H₅ |
| 460 | 4,4-(CH₃)₂-cyclohexyl | C₂H₅ |
| 461 | 4-(CH₃)₃C-cyclohexyl | C₂H₅ |
| 462 | n-C₃H₇ | CF₃CH₂ |
| 463 | i-C₃H₇ | CF₃CH₂ |
| 464 | n-C₄H₉ | CF₃CH₂ |
| 465 | t-C₄H₉ | CF₃CH₂ |
| 466 | CH₂=CHCH₂ | CF₃CH₂ |
| 467 | CH₂=C(CH₃)CH₂ | CF₃CH₂ |
| 468 | CF₃CH₂ | CF₃CH₂ |
| 469 | CF₃CH₂CH₂ | CF₃CH₂ |
| 470 | CF₃CH₂CH₂CH₂ | CF₃CH₂ |
| 471 | CF₃(CH₃)CH | CF₃CH₂ |
| 472 | (S)-CF₃(CH₃)CH | CF₃CH₂ |
| 473 | (R)-CF₃(CH₃)CH | CF₃CH₂ |
| 474 | cyclo-C₃H₅ | CF₃CH₂ |
| 475 | cyclo-C₄H₇ | CF₃CH₂ |
| 476 | cyclo-C₅H₉ | CF₃CH₂ |
| 477 | cyclo-C₆H₁₁ | CF₃CH₂ |
| 478 | cyclo-C₃H₅CH₂ | CF₃CH₂ |
| 479 | cyclo-C₄H₇CH₂ | CF₃CH₂ |
| 480 | cyclo-C₆H₁₁CH₂ | CF₃CH₂ |
| 481 | CH₃CH₂(CH₃)CH | CF₃CH₂ |
| 482 | (S)-CH₃CH₂(CH₃)CH | CF₃CH₂ |
| 483 | (R)-CH₃CH₂(CH₃)CH | CF₃CH₂ |
| 484 | cyclo-C₇H₁₃ | CF₃CH₂ |
| 485 | CH₂=C(CH₃)CH₂ | CF₃CH₂ |
| 486 | CF₃CH₂ | CF₃CH₂ |
| 487 | 4-t-C₄H₉—C₆H₄NH | CF₃CH₂ |
| 488 | 4-F—C₆H₄NH | CF₃CH₂ |
| 489 | C₆H₅NH | CF₃CH₂ |
| 490 | 4-CH₃—C₆H₄NH | CF₃CH₂ |
| 491 | 4-Br—C₆H₄NH | CF₃CH₂ |
| 492 | 2-F—C₆H₄NH | CF₃CH₂ |
| 493 | 3,4-Cl₂—C₆H₃NH | CF₃CH₂ |
| 494 | 3-CF₃—C₆H₄NH | CF₃CH₂ |
| 495 | 3,5-Cl₂—C₆H₃NH | CF₃CH₂ |
| 496 | 4-CF₃O—C₆H₅NH | CF₃CH₂ |
| 497 | 2-CF₃—C₆H₄NH | CF₃CH₂ |
| 498 | 4-CF₃—C₆H₄NH | CF₃CH₂ |
| 499 | 2-Br—C₆H₄NH | CF₃CH₂ |
| 500 | 2-Cl—C₆H₄NH | CF₃CH₂ |
| 501 | 2-CH₃-4-Cl—C₆H₃NH | CF₃CH₂ |
| 502 | 2-CH₃-5-F—C₆H₃NH | CF₃CH₂ |
| 503 | 3-Cl—C₆H₄NH | CF₃CH₂ |
| 504 | (CH₃)₂CHCH₂ | CF₃CH₂ |
| 505 | (CH₃)₃CCH₂ | CF₃CH₂ |
| 506 | (CH₃)₃C(CH₃)CH | CF₃CH₂ |
| 507 | CH₃CH₂(CH₃)₂C | CF₃CH₂ |
| 508 | CH₃CH₂(CF₃)CH | CF₃CH₂ |
| 509 | (S)-CH₃CH₂(CF₃)CH | CF₃CH₂ |
| 510 | (R)-CH₃CH₂(CF₃)CH | CF₃CH₂ |
| 511 | CH₃CH₂(CH₃CH₂)CH | CF₃CH₂ |
| 512 | (CH₃)₂CH(CH₃CH₂)CH | CF₃CH₂ |
| 513 | (CH₃)₂CH(CH₃)CH | CF₃CH₂ |
| 514 | (CH₃)₂CH(CF₃)CH | CF₃CH₂ |
| 515 | (S)-(CH₃)₂CH(CF₃)CH | CF₃CH₂ |
| 516 | (R)-(CH₃)₂CH(CF₃)CH | CF₃CH₂ |
| 517 | HC≡C(CH₃)CH₂ | CF₃CH₂ |
| 518 | CH₂=CH(CH₃CH₂)CH | CF₃CH₂ |
| 520 | CH₃CH₂CH₂(CH₃)CH | CF₃CH₂ |
| 521 | CH₃CH₂CH₂(CF₃)CH | CF₃CH₂ |
| 522 | (S)-CH₃CH₂CH₂(CF₃)CH | CF₃CH₂ |
| 523 | (R)-CH₃CH₂CH₂(CF₃)CH | CF₃CH₂ |
| 524 | CH₃CH₂CH₂(CH₃)₂C | CF₃CH₂ |
| 525 | CH₃CH₂(CH₃)CHCH₂ | CF₃CH₂ |
| 526 | (CH₃)₂CHCH₂CH₂ | CF₃CH₂ |
| 527 | (CH₃)₃CCH₂CH₂ | CF₃CH₂ |
| 528 | CH₃CH₂(CH₃)CH(CH₃)—CH | CF₃CH₂ |
| 529 | CH₃CH₂(CH₃)CH(CF₃)—CH | CF₃CH₂ |
| 530 | (S)-CH₃CH₂(CH₃)CH—(CF₃)CH | CF₃CH₂ |
| 531 | (R)-CH₃CH₂(CH₃)CH—(CF₃)CH | CF₃CH₂ |
| 532 | CH₃(CH₃)CHCH₂(CH₃)—CH | CF₃CH₂ |
| 533 | CH₃(CH₃)CHCH₂(CF₃)—CH | CF₃CH₂ |
| 534 | (S)-CH₃(CH₃)CHCH₂—(CF₃)CH | CF₃CH₂ |
| 535 | (R)-CH₃(CH₃)CHCH₂—(CF₃)CH | CF₃CH₂ |
| 536 | (CH₃)₂CH(CH₃)CH—(CH₃)CH₂ | CF₃CH₂ |
| 537 | (CH₃)₃CCH₂(CH₃)CH | CF₃CH₂ |
| 538 | E-CH₃CH=CH₂ | CF₃CH₂ |
| 539 | E-CH₃CH=CH(CH₃CH₂)—CH | CF₃CH₂ |
| 540 | CH₃CH₂CH₂(CH₃CH₂)—CH | CF₃CH₂ |
| 541 | CH₃CH₂(CH₃CH₂)CH—CH₂ | CF₃CH₂ |
| 542 | CF₂=CFCH₂CH₂ | CF₃CH₂ |
| 543 | CF₃CH₂(CH₃)CHCH₂ | CF₃CH₂ |
| 544 | CF₃CF₂CH₂CH₂ | CF₃CH₂ |
| 545 | CF₃CF₂CF₂CH₂ | CF₃CH₂ |
| 546 | CF₂=C(CH₃)CH₂CH₂ | CF₃CH₂ |
| 547 | CH₃CH₂CH₂CH₂ | CF₃CH₂ |
| 548 | CH₃CH₂CH₂CH₂(CH₃)—CH | CF₃CH₂ |
| 549 | CH₃CH₂(CH₃)CH—CH₂ | CF₃CH₂ |
| 550 | CH₃CH₂(CH₃)CHCH₂—CH₂ | CF₃CH₂ |
| 551 | CH₃CH₂CH₂(CH₃)CH—(CH₃)CH | CF₃CH₂ |
| 552 | CH₃CH₂(CH₃)CHCH₂—(CH₃)CH | CF₃CH₂ |
| 553 | HOCH₂CH₂ | CF₃CH₂ |
| 554 | CH₃OCH₂CH₂ | CF₃CH₂ |
| 555 | CH₃OCH₂(CH₃)CH | CF₃CH₂ |
| 556 | CH₃OCH₂(CF₃)CH | CF₃CH₂ |
| 557 | CH₃OCH₂(CH₃)₂C | CF₃CH₂ |
| 558 | CH₃O(CH₃)CHCH₂ | CF₃CH₂ |

TABLE 1-continued (1A)

| Cmpd No | R³ | R⁴ |
|---|---|---|
| 559 | CH₃O(CH₃)CH(CH₃)CH | CF₃CH₂ |
| 560 | HC≡CCH₂ | CF₃CH₂ |
| 561 | CH₃C≡CCH₂ | CF₃CH₂ |
| 562 | HC≡CCH₂CH₂ | CF₃CH₂ |
| 563 | HOCH₂CH₂CH₂ | CF₃CH₂ |
| 564 | CH₃OCH₂CH₂CH₂ | CF₃CH₂ |
| 565 | (CH₃)₃SiCH₂ | CF₃CH₂ |
| 566 | C₆H₅CH₂ | CF₃CH₂ |
| 567 | C₆H₅(CH₃)CH | CF₃CH₂ |
| 568 | 4-F—C₆H₄CH₂ | CF₃CH₂ |
| 569 | 4-Cl—C₆H₄CH₂ | CF₃CH₂ |
| 570 | 4-F—C₆H₅(CH₃)CH | CF₃CH₂ |
| 571 | 4-Cl—C₆H₅(CH₃)CH | CF₃CH₂ |
| 572 | C₆H₅CH₂CH₂ | CF₃CH₂ |
| 573 | 4-F—C₆H₅CH₂CH₂ | CF₃CH₂ |
| 574 | 1-piperidino | CF₃CH₂ |
| 575 | 1-pyrrolidino | CF₃CH₂ |
| 576 | cyclo-C₅H₉CH₂ | CF₃CH₂ |
| 577 | bicyclo[2.2.1]hept-2-yl | CF₃CH₂ |
| 578 | 1-CH₃-cyclopropyl | CF₃CH₂ |
| 579 | cis-2-CH₃-cyclopropyl | CF₃CH₂ |
| 580 | trans-2-CH₃-cyclopropyl | CF₃CH₂ |
| 581 | 2,2-(CH₃)₂-cyclopropyl | CF₃CH₂ |
| 582 | 1-CH₃-cyclobutyl | CF₃CH₂ |
| 583 | cis-2-CH₃-cyclobutyl | CF₃CH₂ |
| 584 | trans-2-CH₃-cyclobutyl | CF₃CH₂ |
| 585 | cis-3-CH₃-cyclobutyl | CF₃CH₂ |
| 586 | trans-3-CH₃-cyclobutyl | CF₃CH₂ |
| 587 | 2,2-(CH₃)₂-cyclobutyl | CF₃CH₂ |
| 588 | 3,3-(CH₃)₂-cyclobutyl | CF₃CH₂ |
| 589 | 1-CH₃-cyclopentyl | CF₃CH₂ |
| 590 | cis-2-CH₃-cyclopentyl | CF₃CH₂ |
| 591 | trans-2-CH₃-cyclopentyl | CF₃CH₂ |
| 592 | cis-3-CH₃-cyclopentyl | CF₃CH₂ |
| 593 | trans-3-CH₃-cyclopentyl | CF₃CH₂ |
| 594 | 2,2-(CH₃)₂-cyclopentyl | CF₃CH₂ |
| 595 | 3,3-(CH₃)₂-cyclopentyl | CF₃CH₂ |
| 596 | 1-CH₃-cyclohexyl | CF₃CH₂ |
| 597 | cis-2-CH₃-cyclohexyl | CF₃CH₂ |
| 598 | trans-2-CH₃-cyclohexyl | CF₃CH₂ |
| 599 | cis-3-CH₃-cyclohexyl | CF₃CH₂ |
| 600 | trans-3-CH₃-cyclohexyl | CF₃CH₂ |
| 601 | 2,2-(CH₃)₂-cyclohexyl | CF₃CH₂ |
| 602 | 3,3-(CH₃)₂-cyclohexyl | CF₃CH₂ |
| 603 | cis-4-CH₃-cyclohexyl | CF₃CH₂ |
| 604 | trans-4-CH₃-cyclohexyl | CF₃CH₂ |
| 605 | 4,4-(CH₃)₂-cyclohexyl | CF₃CH₂ |
| 606 | 4-(CH₃)₃C-cyclohexyl | CF₃CH₂ |
| 607 | cis-1-CH₃-2-fluorocyclopropyl | H |
| 608 | trans-1-CH₃-2-fluorocyclopropyl | H |
| 609 | 1-CH₃-2,2-difluorocyclopropyl | H |
| 610 | cis-1-CH₃-2-chloro-2-fluorocyclopropyl | H |
| 611 | trans-1-CH₃-2-chloro-2-fluorocyclopropyl | H |
| 612 | CH₃CO(CH₃)CH | H |
| 613 | CH₃CH₂CO(CH₃)CH | H |
| 614 | (CH₃)₂CHCO(CH₃)CH | H |
| 615 | (CH₃)₃CCO(CH₃)CH | H |
| 616 | CH₃CH₂CH₂CO(CH₃)CH | H |
| 617 | CH₃CO(CF₃)CH | H |
| 618 | CH₃CH₂CO(CF₃)CH | H |
| 619 | CH₃CO(CH₃)₂C | H |
| 620 | CH₃CH₂CO(CH₃)₂C | H |
| 621 | cis-1-CH₃-2-fluorocyclopropyl | CH₃ |
| 622 | trans-1-CH₃-2-fluorocyclopropyl | CH₃ |
| 623 | 1-CH₃-2,2-difluorocyclopropyl | CH₃ |
| 624 | cis-1-CH₃-2-chloro-2-fluorocyclopropyl | CH₃ |
| 625 | trans-1-CH₃-2-chloro-2-fluorocyclopropyl | CH₃ |
| 626 | CH₃CO(CH₃)CH | CH₃ |
| 627 | CH₃CH₂CO(CH₃)CH | CH₃ |
| 628 | (CH₃)₂CHCO(CH₃)CH | CH₃ |
| 629 | (CH₃)₃CCO(CH₃)CH | CH₃ |
| 630 | CH₃CH₂CH₂CO(CH₃)CH | CH₃ |
| 631 | CH₃CO(CF₃)CH | CH₃ |
| 632 | CH₃CH₂CO(CF₃)CH | CH₃ |
| 633 | CH₃CO(CH₃)₂C | CH₃ |
| 634 | CH₃CH₂CO(CH₃)₂C | CH₃ |
| 635 | cis-1-CH₃-2-fluorocyclopropyl | C₂H₅ |
| 636 | trans-1-CH₃-2-fluorocyclopropyl | C₂H₅ |
| 637 | 1-CH₃-2,2-difluorocyclopropyl | C₂H₅ |
| 638 | cis-1-CH₃-2-chloro-2-fluorocyclopropyl | C₂H₅ |
| 639 | trans-1-CH₃-2-chloro-2-fluorocyclopropyl | C₂H₅ |
| 640 | CH₃CO(CH₃)CH | C₂H₅ |
| 641 | CH₃CH₂CO(CH₃)CH | C₂H₅ |
| 642 | (CH₃)₂CHCO(CH₃)CH | C₂H₅ |
| 643 | (CH₃)₃CCO(CH₃)CH | C₂H₅ |
| 644 | CH₃CH₂CH₂CO(CH₃)CH | C₂H₅ |
| 645 | CH₃CO(CF₃)CH | C₂H₅ |
| 646 | CH₃CH₂CO(CF₃)CH | C₂H₅ |
| 647 | CH₃CO(CH₃)₂C | C₂H₅ |
| 648 | CH₃CH₂CO(CH₃)₂C | C₂H₅ |
| 649 | cis-1-CH₃-2-fluorocyclopropyl | CF₃CH₂ |
| 650 | trans-1-CH₃-2-fluorocyclopropyl | CF₃CH₂ |
| 651 | 1-CH₃-2,2-difluorocyclopropyl | CF₃CH₂ |
| 652 | cis-1-CH₃-2-chloro-2-fluorocyclopropyl | CF₃CH₂ |
| 653 | trans-1-CH₃-2-chloro-2-fluorocyclopropyl | CF₃CH₂ |
| 654 | CH₃CO(CH₃)CH | CF₃CH₂ |
| 655 | CH₃CH₂CO(CH₃)CH | CF₃CH₂ |
| 656 | (CH₃)₂CHCO(CH₃)CH | CF₃CH₂ |
| 657 | (CH₃)₃CCO(CH₃)CH | CF₃CH₂ |
| 658 | CH₃CH₂CH₂CO(CH₃)CH | CF₃CH₂ |
| 659 | CH₃CO(CF₃)CH | CF₃CH₂ |
| 660 | CH₃CH₂CO(CF₃)CH | CF₃CH₂ |
| 661 | CH₃CO(CH₃)₂C | CF₃CH₂ |
| 662 | CH₃CH₂CO(CH₃)₂C | CF₃CH₂ |

Table 2

Table 2 consists of 662 compounds of the general formula (1A), where W, X and Y are CH and Z is N, R is Cl, $R^1$ is 2,5,6-trifluorophenyl, and the values of $R^3$ and $R^4$ are as listed in Table 1. Thus, compound 1 of Table 2 is the same as compound 1 of Table 1 except that in compound 1 of Table 2, $R^1$ is 2,5,6-trifluorophenyl. Similarly, compounds 2 to 662 of Table 2 are the same as compounds 2 to 662 of Table 1 except that in the compounds of Table 2, $R^1$ is 2,5,6-trifluorophenyl.

Table 3

Table 3 consists of 662 compounds of the general formula (1A), where W, X and Y are CH and Z is N, R is Cl, $R^1$ is 2,3,4,5,6-pentafluorophenyl, and the values of $R^3$ and $R^4$ are as listed in Table 1. Thus, compound 1 of Table 3 is the same as compound 1 of Table 1 except that in compound 1 of Table 3, $R^1$ is 2,3,4,5,6-pentafluorophenyl. Similarly, compounds 2 to 662 of Table 3 are the same as compounds 2 to 662 of Table 1 except that in the compounds of Table 3, $R^1$ is 2,3,4,5,6-pentafluorophenyl.

Table 4

Table 4 consists of 662 compounds of the general formula (1A), where W, X and Y are CH and Z is N, R is Cl, $R^1$ is 2,6-difluoro-4-methoxyphenyl, and the values of $R^3$ and $R^4$ are as listed in Table 1. Thus, compound 1 of Table 4 is the same as compound 1 of Table 1 except that in compound 1 of Table 4, $R^1$ is 2,6-difluoro-4-methoxyphenyl. Similarly, compounds 2 to 662 of Table 4 are the same as compounds 2 to 662 of Table 1 except that in the compounds of Table 4, $R^1$ is 2,6-difluoro-4-methoxyphenyl.

Table 5

Table 5 consists of 662 compounds of the general formula (1A), where W, X and Y are CH and Z is N, R is Cl, $R^1$ is 2-fluoro-6-chlorophenyl, and the values of $R^3$ and $R^4$ are as listed in Table 1. Thus, compound 1 of Table 5 is the same as compound 1 of Table 1 except that in compound 1 of Table 5, $R^1$ is 2-fluoro-6-chlorophenyl. Similarly, compounds 2 to 662 of Table 5 are the same as compounds 2 to 662 of Table 1 except that in the compounds of Table 5, $R^1$ is 2-fluoro-6-chlorophenyl.

TABLE 6

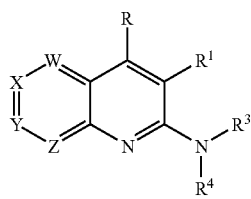

(1B)

Table 6 consists of 662 compounds of the general formula (1B), where W, X and Y are CH and Z is N, R is Cl, $R^1$ is 2,4,6-trifluorophenyl, and the values of $R^3$ and $R^4$ are as listed in Table 1. Thus, compound 1 of Table 6 is the same as compound 1 of Table 1 except that in compound 1 of Table 6, the compound has the general formula (1B). Similarly, compounds 2 to 662 of Table 6 are the same as compounds 2 to 662 of Table 1 except that in the compounds of Table 6, the compounds have the general formula (1B).

Table 7

Table 7 consists of 662 compounds of the general formula (1B), where W, X and Y are CH and Z is N, R is Cl, $R^1$ is 2,5,6-trifluorophenyl, and the values of $R^3$ and $R^4$ are as listed in Table 1. Thus, compound 1 of Table 7 is the same as compound 1 of Table 2 except that in compound 1 of Table 7, the compound has the general formula (1B). Similarly, compounds 2 to 662 of Table 7 are the same as compounds 2 to 662 of Table 2 except that in the compounds of Table 7, the compounds have the general formula (1B).

Table 8

Table 8 consists of 662 compounds of the general formula (1B), where W, X and Y are CH and Z is N, R is Cl, $R^1$ is 2,3,4,5,6-pentafluorophenyl, and the values of $R^3$ and $R^4$ are as listed in Table 3. Thus, compound 1 of Table 8 is the same as compound 1 of Table 3 except that in compound 1 of Table 8, the compound has the general formula (1B). Similarly, compounds 2 to 662 of Table 8 are the same as compounds 2 to 662 of Table 3 except that in the compounds of Table 8, the compounds have the general formula (1B).

Table 9

Table 9 consists of 662 compounds of the general formula (1B), where W, X and Y are CH and Z is N, R is Cl, $R^1$ is 2,6-difluoro-4-methoxyphenyl, and the values of $R^3$ and $R^4$ are as listed in Table 1. Thus, compound 1 of Table 9 is the same as compound 1 of Table 4 except that in compound 1 of Table 9, the compound has the general formula (1B). Similarly, compounds 2 to 662 of Table 9 are the same as compounds 2 to 662 of Table 4 except that in the compounds of Table 9, the compounds have the general formula (1B).

Table 10

Table 10 consists of 662 compounds of the general formula (1B), where W, X and Y are CH and Z is N, R is Cl, $R^1$ is 2-fluoro-6-chlorophenyl, and the values of $R^3$ and $R^4$ are as listed in Table 1. Thus, compound 1 of Table 10 is the same as compound 1 of Table 5 except that in compound 1 of Table 10, the compound has the general formula (1B). Similarly, compounds 2 to 662 of Table 10 are the same as compounds 2 to 662 of Table 5 except that in the compounds of Table 10, the compounds have the general formula (1B).

Table 11

Table 11 consists of 662 compounds of the general formula (1A), where W is N and X, Y and Z are CH, R is Cl, $R^1$ is 2,4,6-trifluorophenyl, and the values of $R^3$ and $R^4$ are as listed in Table 1. Thus, compound 1 of Table 11 is the same as compound 1 of Table 1 except that in compound 1 of Table 11, the compound has the general formula (1A) where W is N and X, Y and Z are CH. Similarly, compounds 2 to 662 of Table 11 are the same as compounds 2 to 662 of Table 1 except that in the compounds of Table 11, the compounds have the general formula (1A) where W is N and X, Y and Z are CH.

Table 12

Table 12 consists of 662 compounds of the general formula (1A), where W is N and X, Y and Z are CH, R is Cl, $R^1$ is 2,5,6-trifluorophenyl, and the values of $R^3$ and $R^4$ are as listed in Table 1. Thus, compound 1 of Table 12 is the same as compound 1 of Table 2 except that in compound 1 of Table 12, the compound has the general formula (1A) where W is N and X, Y and Z are CH. Similarly, compounds 2 to 662 of Table 12 are the same as compounds 2 to 662 of Table 2 except that in the compounds of Table 12, the compounds have the general formula (1A) where W is N and X, Y and Z are CH.

Table 13

Table 13 consists of 662 compounds of the general formula (1A), where W is N and X, Y and Z are CH, R is Cl, $R^1$ is 2,3,4,5,6-pentafluorophenyl, and the values of $R^3$ and $R^4$ are as listed in Table 1. Thus, compound 1 of Table 13 is the same as compound 1 of Table 3 except that in compound 1 of Table 13, the compound has the general formula (1A) where W is N and X, Y and Z are CH. Similarly, compounds 2 to 662 of Table 13 are the same as compounds 2 to 662 of Table 3 except that in the compounds of Table 13, the compounds have the general formula (1A) where W is N and X, Y and Z are CH.

Table 14

Table 14 consists of 662 compounds of the general formula (1A), where W is N and X, Y and Z are CH, R is Cl, $R^1$ is 2,6-difluoro-4-methoxyphenyl, and the values of $R^3$ and $R^4$ are as listed in Table 1. Thus, compound 1 of Table 14 is the same as compound 1 of Table 4 except that in compound 1 of Table 14, the compound has the general formula (1A) where W is N and X, Y and Z are CH. Similarly, compounds 2 to 662 of Table 14 are the same as compounds 2 to 662 of Table 4 except that in the compounds of Table 14, the compounds have the general formula (1A) where W is N and X, Y and Z are CH.

Table 15

Table 15 consists of 662 compounds of the general formula (1A), where W is N and X, Y and Z are CH, R is Cl, $R^1$ is 2-fluoro-6-chlorophenyl, and the values of $R^3$ and $R^4$ are as listed in Table 1. Thus, compound 1 of Table 15 is the same as compound 1 of Table 5 except that in compound 1 of Table 15, the compound has the general formula (1A) where W is N and X, Y and Z are CH. Similarly, compounds 2 to 662 of Table 15 are the same as compounds 2 to 662 of Table 5 except that in the compounds of Table 15, the compounds have the general formula (1A) where W is N and X, Y and Z are CH.

Table 16
Table 16 consists of 662 compounds of the general formula (1B), where W is N and X, Y and Z are CH, R is Cl, $R^1$ is 2,4,6-trifluorophenyl, and the values of $R^3$ and $R^4$ are as listed in Table 1. Thus, compound 1 of Table 16 is the same as compound 1 of Table 11 except that in compound 1 of Table 16, the compound has the general formula (1B). Similarly, compounds 2 to 662 of Table 16 are the same as compounds 2 to 662 of Table 11 except that in the compounds of Table 16, the compounds have the general formula (1B).

Table 17
Table 17 consists of 662 compounds of the general formula (1B), where W is N and X, Y and Z are CH, R is Cl, $R^1$ is 2,5,6-trifluorophenyl, and the values of $R^3$ and $R^4$ are as listed in Table 1. Thus, compound 1 of Table 17 is the same as compound 1 of Table 12 except that in compound 1 of Table 17, the compound has the general formula (1B). Similarly, compounds 2 to 662 of Table 17 are the same as compounds 2 to 662 of Table 12 except that in the compounds of Table 17, the compounds have the general formula (1B).

Table 18
Table 18 consists of 662 compounds of the general formula (1B), where W is N and X, Y and Z are CH, R is Cl, $R^1$ is 2,3,4,5,6-pentafluorophenyl, and the values of $R^3$ and $R^4$ are as listed in Table 1. Thus, compound 1 of Table 18 is the same as compound 1 of Table 13 except that in compound 1 of Table 18, the compound has the general formula (1B). Similarly, compounds 2 to 662 of Table 18 are the same as compounds 2 to 662 of Table 13 except that in the compounds of Table 18, the compounds have the general formula (1B).

Table 19
Table 19 consists of 662 compounds of the general formula (1B), where W is N and X, Y and Z are CH, R is Cl, $R^1$ is 2,6-difluoromethoxyphenyl, and the values of $R^3$ and $R^4$ are as listed in Table 1. Thus, compound 1 of Table 19 is the same as compound 1 of Table 14 except that in compound 1 of Table 19, the compound has the general formula (1B). Similarly, compounds 2 to 662 of Table 19 are the same as compounds 2 to 662 of Table 14 except that in the compounds of Table 19, the compounds have the general formula (1B).

Table 20
Table 20 consists of 662 compounds of the general formula (1B), where W is N and X, Y and Z are CH, R is Cl, $R^1$ is 2-fluoro-6-chlorophenyl, and the values of $R^3$ and $R^4$ are as listed in Table 1. Thus, compound 1 of Table 20 is the same as compound 1 of Table 15 except that in compound 1 of Table 20, the compound has the general formula (1B). Similarly, compounds 2 to 662 of Table 20 are the same as compounds 2 to 662 of Table 15 except that in the compounds of Table 20, the compounds have the general formula (1B).

Table 21
Table 21 consists of 662 compounds of the general formula (1A), where W, X and Z are CH and Y is N, R is Cl, $R^1$ is 2,4,6-trifluorophenyl, and the values of $R^3$ and $R^4$ are as listed in Table 1. Thus, compound 1 of Table 21 is the same as compound 1 of Table 1 except that in compound 1 of Table 21, the compound has the general formula (1A) where W, X and Z are CH and Y is N. Similarly, compounds 2 to 662 of Table 21 are the same as compounds 2 to 662 of Table 1 except that in the compounds of Table 21, the compounds have the general formula (1A) where W, X and Z are CH and Y is N.

Table 22
Table 22 consists of 662 compounds of the general formula (1A), where W, X and Z are CH and Y is N, R is Cl, $R^1$ is 2,5,6-trifluorophenyl, and the values of $R^3$ and $R^4$ are as listed in Table 1. Thus, compound 1 of Table 22 is the same as compound 1 of Table 2 except that in compound 1 of Table 22, the compound has the general formula (1A) where W, X and Z are CH and Y is N. Similarly, compounds 2 to 662 of Table 22 are the same as compounds 2 to 662 of Table 2 except that in the compounds of Table 22, the compounds have the general formula (1A) where W, X and Z are CH and Y is N.

Table 23
Table 23 consists of 662 compounds of the general formula (1A), where W, X and Z are CH and Y is N, R is Cl, $R^1$ is 2,3,4,5,6-pentafluorophenyl, and the values of $R^3$ and $R^4$ are as listed in Table 1. Thus, compound 1 of Table 23 is the same as compound 1 of Table 3 except that in compound 1 of Table 23, the compound has the general formula (1A) where W, X and Z are CH and Y is N. Similarly, compounds 2 to 662 of Table 23 are the same as compounds 2 to 662 of Table 3 except that in the compounds of Table 23, the compounds have the general formula (1A) where W, X and Z are CH and Y is N.

Table 24
Table 24 consists of 662 compounds of the general formula (1A), where W, X and Z are CH and Y is N, R is Cl, $R^1$ is 2,6-difluoro-4-methoxyphenyl, and the values of $R^3$ and $R^4$ are as listed in Table 1. Thus, compound 1 of Table 24 is the same as compound 1 of Table 4 except that in compound 1 of Table 24, the compound has the general formula (1A) where W, X and Z are CH and Y is N. Similarly, compounds 2 to 662 of Table 24 are the same as compounds 2 to 662 of Table 4 except that in the compounds of Table 24, the compounds have the general formula (1A) where W, X and Z are CH and Y is N.

Table 25
Table 25 consists of 662 compounds of the general formula (1A), where W, X and Z are CH and Y is N, R is Cl, $R^1$ is 2-fluoro-6-chlorophenyl, and the values of $R^3$ and $R^4$ are as listed in Table 1. Thus, compound 1 of Table 25 is the same as compound 1 of Table 5 except that in compound 1 of Table 25, the compound has the general formula (1A) where W, X and Z are CH and Y is N. Similarly, compounds 2 to 662 of Table 25 are the same as compounds 2 to 662 of Table 5 except that in the compounds of Table 25, the compounds have the general formula (1A) where W, X and Z are CH and Y is N.

Table 26
Table 26 consists of 662 compounds of the general formula (1A), where W, Y and Z are CH and X is N, R is Cl, $R^1$ is 2,4,6-trifluorophenyl, and the values of $R^3$ and $R^4$ are as listed in Table 1. Thus, compound 1 of Table 26 is the same as compound 1 of Table 1 except that in compound 1 of Table 26, the compound has the general formula (1A) where W, Y and Z are CH and X is N. Similarly, compounds 2 to 662 of Table 26 are the same as compounds 2 to 662 of Table 1 except that in the compounds of Table 26, the compounds have the general formula (1A) where W, Y and Z are CH and X is N.

Table 27
Table 27 consists of 662 compounds of the general formula (1A), where W, Y and Z are CH and X is N, R is Cl, $R^1$ is 2,5,6-trifluorophenyl, and the values of $R^3$ and $R^4$ are as listed in Table 1. Thus, compound 1 of Table 27 is the same as compound 1 of Table 2 except that in compound 1 of Table 27, the compound has the general formula (1A) where W, Y and Z are CH and X is N. Similarly, compounds 2 to 662 of Table 27 are the same as compounds 2 to 662 of Table 2 except that in the compounds of Table 27, the compounds have the general formula (1A) where W, Y and Z are CH and X is N.

Table 28
Table 28 consists of 662 compounds of the general formula (1A), where W, Y and Z are CH and X is N, R is Cl, $R^1$ is 2,3,4,5,6-pentafluorophenyl, and the values of $R^3$ and $R^4$ are as listed in Table 1. Thus, compound 1 of Table 28 is the same as compound 1 of Table 3 except that in compound 1 of Table 28, the compound has the general formula (1A) where W, Y and Z are CH and X is N. Similarly, compounds 2 to 662 of Table 28 are the same as compounds 2 to 662 of Table 3 except that in the compounds of Table 28, the compounds have the general formula (1A) where W, Y and Z are CH and X is N.

Table 29

Table 29 consists of 662 compounds of the general formula (1A), where W, Y and Z are CH and X is N, R is Cl, $R^1$ is 2,6-difluoro-4-methoxyphenyl, and the values of $R^3$ and $R^4$ are as listed in Table 1. Thus, compound 1 of Table 29 is the same as compound 1 of Table 4 except that in compound 1 of Table 29, the compound has the general formula (1A) where W, Y and Z are CH and X is N. Similarly, compounds 2 to 662 of Table 29 are the same as compounds 2 to 662 of Table 4 except that in the compounds of Table 29, the compounds have the general formula (1A) where W, Y and Z are CH and X is N.

Table 30

Table 30 consists of 662 compounds of the general formula (1A), where W, Y and Z are CH and X is N, R is Cl, $R^1$ is 2-fluoro-6-chlorophenyl, and the values of $R^3$ and $R^4$ are as listed in Table 1. Thus, compound 1 of Table 30 is the same as compound 1 of Table 5 except that in compound 1 of Table 30, the compound has the general formula (1A) where W, Y and Z are CH and X is N. Similarly, compounds 2 to 662 of Table 30 are the same as compounds 2 to 662 of Table 5 except that in the compounds of Table 30, the compounds have the general formula (1A) where W, Y and Z are CH and X is N.

Table 31

Table 31 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 31 $R^1$ is 2,6-difluorophenyl instead of 2-fluoro-6-chlorophenyl.

Table 32

Table 32 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 32 $R^1$ is 2-fluorophenyl instead of 2-fluoro-6-chlorophenyl.

Table 33

Table 33 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 33 $R^1$ is 2,3,5,6-tetrafluorophenyl instead of 2-fluoro-6-chlorophenyl.

Table 34

Table 34 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 34 $R^1$ is 2-chloro-4,6-difluorophenyl instead of 2-fluoro-6-chlorophenyl.

Table 35

Table 35 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 35 $R^1$ is 2-chlorophenyl instead of 2-fluoro-6-chlorophenyl.

Table 36

Table 36 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 36 $R^1$ is 2,6-dichlorophenyl instead of 2-fluoro-6-chlorophenyl.

Table 37

Table 37 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 37 $R^1$ is 2,4-dichlorophenyl instead of 2-fluoro-6-chlorophenyl.

Table 38

Table 38 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 38 $R^1$ is 2,4,6-trichlorophenyl instead of 2-fluoro-6-chlorophenyl.

Table 39

Table 39 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 39 $R^1$ is 2,3,6-trichlorophenyl instead of 2-fluoro-6-chlorophenyl.

Table 40

Table 40 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 40 $R^1$ is pentachlorophenyl instead of 2-fluoro-6-chlorophenyl.

Table 41

Table 41 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 41 $R^1$ is 2-fluoro-4,6-dichlorophenyl instead of 2-fluoro-6-chlorophenyl.

Table 42

Table 42 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 42 $R^1$ is 4-fluoro-2,6-dichlorophenyl instead of 2-fluoro-6-chlorophenyl.

Table 43

Table 43 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 43 $R^1$ is 2-bromophenyl instead of 2-fluoro-6-chlorophenyl.

Table 44

Table 44 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 44 $R^1$ is 2-fluoro-6-bromophenyl instead of 2-fluoro-6-chlorophenyl.

Table 45

Table 45 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds to 662 of Table 20 respectively, compounds 2649 to 310 are exactly the same as compounds 1 to 662 of Table 25 respectively, and compounds 3311 to 3972 are exactly the same as compounds 1 to 662 of Table 30 respectively, except that in all of the compounds of Table 45 $R^1$ is 2-bromo-4,6-difluorophenyl instead of 2-fluoro-6-chlorophenyl.

Table 46

Table 46 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 46 $R^1$ is 2-fluoro-6-methylphenyl instead of 2-fluoro-6-chlorophenyl.

Table 47

Table 47 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 47 $R^1$ is 2-chloro-6-methylphenyl instead of 2-fluoro-6-chlorophenyl.

Table 48

Table 48 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 48 $R^1$ is 2-methoxyphenyl instead of 2-fluoro-6-chlorophenyl.

Table 49

Table 49 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the sane as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 49 $R^1$ is 2,6-dimethoxyphenyl instead of 2-fluoro-6-chlorophenyl.

Table 50

Table 50 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 50 $R^1$ is 2-fluoro-6-methoxyphenyl instead of 2-fluoro-6-chlorophenyl.

Table 51

Table 51 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 51 $R^1$ is 2-trifluoromethylphenyl instead of 2-fluoro-6-chlorophenyl.

Table 52

Table 52 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 52 $R^1$ is 2-fluoro-6-trifluoromethylphenyl instead of 2-fluoro-6-chlorophenyl.

Table 53

Table 53 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 53 $R^1$ is 2,6-di-(trifluoromethyl)phenyl instead of 2-fluoro-6-chlorophenyl.

Table 54

Table 54 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 54 $R^1$ is 2-chloro-6-trifluoromethylphenyl instead of 2-fluoro-6-chlorophenyl.

Table 55

Table 55 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 55 $R^1$ is 2,4-difluoro-6-trifluoromethylphenyl instead of 2-fluoro-6-chlorophenyl.

Table 56

Table 56 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 56 $R^1$ is 2,4-difluoro-6-methoxyphenyl instead of 2-fluoro-6-chlorophenyl.

Table 57

Table 57 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 57 $R^1$ is 2,4-difluoro-6-methylphenyl instead of 2-fluoro-6-chlorophenyl.

Table 58

Table 58 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 58 $R^1$ is 2,4-difluoropyrid-3-yl instead of 2-fluoro-6-chlorophenyl.

Table 59

Table 59 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 59 $R^1$ is 3,5-difluoropyrid-4-yl instead of 2-fluoro-6-chlorophenyl.

Table 60

Table 60 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 60 $R^1$ is tetrafluoropyrid-4-yl instead of 2-fluoro-6-chlorophenyl.

Table 61

Table 61 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 61 $R^1$ is 3-fluoropyrid-2-yl instead of 2-fluoro-6-chlorophenyl.

Table 62

Table 62 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 62 $R^1$ is 4-fluoropyrid-3-yl instead of 2-fluoro-6-chlorophenyl.

Table 63

Table 63 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 63 $R^1$ is 3-fluoropyrid-4-yl instead of 2-fluoro-6-chlorophenyl.

Table 64

Table 64 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 64 $R^1$ is 2-fluoropyrid-3-yl instead of 2-fluoro-6-chlorophenyl.

Table 65

Table 65 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 65 $R^1$ is 2,4,6-trifluoropyrid-3-yl instead of 2-fluoro-6-chlorophenyl.

Table 66

Table 66 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 66 $R^1$ is 3,5-difluoropyrid-2-yl instead of 2-fluoro-6-chlorophenyl.

Table 67

Table 67 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 67 R¹ is 2,6-difluoropyrid-3-yl instead of 2-fluoro-6-chlorophenyl.
Table 68
Table 68 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 68 R¹ is 2,4-difluoro-6-methoxypyrid-3-yl instead of 2-fluoro-6-chlorophenyl.
Table 69
Table 69 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 69 R¹ is 2-fluoro-4-chloropyrid-3-yl instead of 2-fluoro-6-chlorophenyl.
Table 70
Table 70 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 70 R¹ is 3-fluoro-5-chloropyrid-4-yl instead of 2-fluoro-6-chlorophenyl.
Table 71
Table 71 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 71 R¹ is 2-chloro-4-fluoropyrid-3-yl instead of 2-fluoro-6-chlorophenyl.
Table 72
Table 72 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 72 R¹ is 2,4-dichloropyrid-3-yl instead of 2-fluoro-6-chlorophenyl.
Table 73
Table 73 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 73 R¹ is 3-chloropyrid-2-yl instead of 2-fluoro-6-chlorophenyl.
Table 74
Table 74 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table-25 respectively, and compounds 3311 to 3972 are exactly the same as compounds 1 to 662 of Table 30 respectively, except that in all of the compounds of Table 74 R¹ is 4-chloropyrid-3-yl instead of 2-fluoro-6-chlorophenyl.
Table 75
Table 75 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively; compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 75 R¹ is 3-chloropyrid-4-yl instead of 2-fluoro-6-chlorophenyl.
Table 76
Table 76 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 76 R¹ is 2-chloropyrid-3-yl instead of 2-fluoro-6-chlorophenyl.
Table 77
Table 77 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 77 R¹ is 3-trifluoromethylpyrid-2-yl instead of 2-fluoro-6-chlorophenyl.

Table 78

Table 78 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 78 R¹ is 4-trifluoromethylpyrid-3-yl instead of 2-fluoro-6-chlorophenyl.

Table 79

Table 79 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 79 R¹ is 3,5-dichloropyrid-2-yl instead of 2-fluoro-6-chlorophenyl.

Table 80

Table 80 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 80 R¹ is 4,6-dichloropyrid-3-yl instead of 2-fluoro-6-chlorophenyl.

Table 81

Table 81 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 81 R¹ is 3-trifluoromethylpyrid-4-yl instead of 2-fluoro-6-chlorophenyl.

Table 82

Table 82 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 82 R¹ is 2-trifluoromethylpyrid-3-yl instead of 2-fluoro-6-chlorophenyl.

Table 83

Table 83 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 83 R¹ is 2-fluoro-4-trifluoromethylpyrid-3-yl instead of 2-fluoro-6-chlorophenyl.

Table 84

Table 84 consists of 3972 compounds. Compounds 1 to 662 are exactly the same as compounds 1 to 0.662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 84 R¹ is 3-fluoro-5-trifluoromethylpyrid-4-yl instead of 2-fluoro-6-chlorophenyl.

Table 85

Table 85 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 85 R¹ is 4-fluoro-2-trifluoromethylpyrid-3-yl instead of 2-fluoro-6-chlorophenyl.

Table 86

Table 86 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 86 R¹ is 2,6-dichloropyrid-3-yl instead of 2-fluoro-6-chlorophenyl.

Table 87

Table 87 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 87 $R^1$ is 3,5-dichloropyrid-4-yl instead of 2-fluoro-6-chlorophenyl.

Table 88

Table 88 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 88 $R^1$ is 3-chloro-6-trifluoromethylpyrid-2-yl instead of 2-fluoro-6-chlorophenyl.

Table 89

Table 89 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 89 $R^1$ is 3-fluoro-6-trifluoromethylpyrid-2-yl instead of 2-fluoro-6-chlorophenyl.

Table 90

Table 90 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 90 $R^1$ is pyrid-2-yl instead of 2-fluoro-6-chlorophenyl.

Table 91

Table 91 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 91 $R^1$ is pyrid-3-yl instead of 2-fluoro-6-chlorophenyl.

Table 92

Table 92 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 92 $R^1$ is pyrid-4-yl instead of 2-fluoro-6-chlorophenyl.

Table 93

Table 93 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 93 $R^1$ is 3-fluorothien-2-yl instead of 2-fluoro-6-chlorophenyl.

Table 94

Table 94 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 94 $R^1$ is 3-chlorothien-2-yl instead of 2-fluoro-6-chlorophenyl.

Table 95

Table 95 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 95 $R^1$ is 2,4-difluorothien-3-yl instead of 2-fluoro-6-chlorophenyl.

Table 96

Table 96 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 96 $R^1$ is 2,4-dichlorothien-3-yl instead of 2-fluoro-6-chlorophenyl.

Table 97

Table 97 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 97 $R^1$ is 2,4,5-trichlorothien-3-yl instead of 2-fluoro-6-chlorophenyl.

Table 98

Table 98 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 98 $R^1$ is piperidino instead of 2-fluoro-6-chlorophenyl.

Table 99

Table 99 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 99 $R^1$ is 2-methylpiperidino instead of 2-fluoro-6-chlorophenyl.

Table 100

Table 100 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 100 $R^1$ is 2,6-dimethylpiperidino instead of 2-fluoro-6-chlorophenyl.

Table 101

Table 101 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 39.72 are exactly the same as compounds 1 to 662 of Table 30 respectively, except that in all of the compounds of Table 101 $R^1$ is morpholino instead of 2-fluoro-6-chlorophenyl.

Table 102

Table 102 consists of 3972 compounds. Compounds 1 to 662 are exactly the same as compounds 1 to 662 of Table 5 respectively, compounds 663 to 1324 are exactly the same as compounds 1 to 662 of Table 10 respectively, compounds 1325 to 1986 are exactly the same as compounds 1 to 662 of Table 15 respectively, compounds 1987 to 2648 are exactly the same as compounds 1 to 662 of Table 20 respectively, compounds 2649 to 3310 are exactly the same as compounds 1 to 662 of Table 25 respectively, and compounds 3311 to 3972 are exactly the same as compounds 1 to 662 of Table 30 respectively, except that in all of the compounds of Table 102 $R^1$ is 2,6-dimethylmorpholino instead of 2-fluoro-6-chlorophenyl.

Table 103

Table 103 consists of 305,844 compounds. Each of these compounds is exactly the same as the corresponding compound in Tables 1 to 102 (thus, for example, compound 1 of Table 103 is the same as compound 1 of Table 1, compound 663 of Table 103 is the same as compound 1 of Table 2, compound 19,861 of Table 103 is the same as compound 1 of Table 31, compound 305,844 of Table 103 is the same as compound 3,972 of Table 102) except that in all of the compounds of Table 103 R is F instead of Cl.

Table 104

Table 104 consists of 305,844 compounds. Each of these compounds is exactly the same as the corresponding compound in Tables 1 to 102 (thus, for example, compound 1 of Table 104 is the same as compound 1 of Table 1, compound 663 of Table 104 is the same as compound 1 of Table 2, compound 19,861 of Table 104 is the same as compound 1 of Table 31, compound 305,844 of Table 104 is the same as compound 3,972 of Table 102) except that in all of the compounds of Table 104 R is Br instead of Cl.

Table 105

Table 105 consists of 305,844 compounds. Each of these compounds is exactly the same as the corresponding compound in Tables 1 to 102 (thus, for example, compound 1 of Table 105 is the same as compound 1 of Table 1, compound 663 of Table 105 is the same as compound 1 of Table 2, compound 19,861 of Table 105 is the same as compound 1 of Table 31, compound 305,844 of Table 105 is the same as compound 3,972 of Table 102) except that in all of the compounds of Table 105 R is methyl instead of Cl.

Table 106

Table 106 consists of 305,844 compounds. Each of these compounds is exactly the same as the corresponding compound in Tables 1 to 102 (thus, for example, compound 1 of Table 106 is the same as compound 1 of Table 1, compound 663 of Table 106 is the same as compound 1 of Table 2, compound 19,861 of Table 106 is the same as compound 1 of Table 31, compound 305,844 of Table 106 is the same as compound 3,972 of Table 102) except that in all of the compounds of Table 106 R is ethyl instead of Cl.

Table 107

Table 107 consists of 305,844 compounds. Each of these compounds is exactly the same as the corresponding compound in Tables 1 to 102 (thus, for example, compound 1 of Table 107 is the same as compound 1 of Table 1, compound 663 of Table 107 is the same as compound 1 of Table 2, compound 19,861 of Table 107 is the same as compound 1 of Table 31, compound 305,844 of Table 107 is the same as compound 3,972 of Table 102) except that in all of the compounds of Table 107 R is cyano instead of Cl.

Table 108

Table 108 consists of 305,844 compounds. Each of these compounds is exactly the same as the corresponding compound in Tables 1 to 102 (thus, for example, compound 1 of Table 108 is the same as compound 1 of Table 1, compound 663 of Table 108 is the same as compound 1 of Table 2, compound 19,861 of Table 108 is the same as compound 1 of Table 31, compound 305,844 of Table 108 is the same as compound 3,972 of Table 102) except that in all of the compounds of Table 108 R is methoxy instead of Cl.

Table 109

Table 109 consists of 6620 compounds. Each of these compounds is exactly the same as the corresponding compound in Tables 1 to 10 (thus, for example, compound 1 of Table 109 is the same as compound 1 of Table 1, compound 663 of Table 109 is the same as compound 1 of Table 2, etc.) except that in all of the compounds of Table 109 X is CF instead of CH.

Table 110

Table 110 consists of 6620 compounds. Each of these compounds is exactly the same as the corresponding compound in Tables 1 to 10 (thus, for example, compound 1 of Table 110 is the same as compound 1 of Table 1, compound 663 of Table 110 is the same as compound 1 of Table 2, etc.) except that in all of the compounds of Table 110 X is CCl instead of CH.

Table 111

Table 111 consists of 6620 compounds. Each of these compounds is exactly the same as the corresponding compound in Tables 1 to 10 (thus, for example, compound 1 of Table 111 is the same as compound 1 of Table 1, compound 663 of Table 111 is the same as compound 1 of Table 2, etc.) except that in all of the compounds of Table 111 X is CBr instead of CH.

Table 112

Table 112 consists of 6620 compounds. Each of these compounds is exactly the same as the corresponding compound in Tables 1 to 10 (thus, for example, compound 1 of Table 112 is the same as compound 1 of Table 1, compound 663 of Table 112 is the same as compound 1 of Table 2, etc.) except that in all of the compounds of Table 112 X is $CCH_3$ instead of CH.

Table 113

Table 113 consists of 6620 compounds. Each of these compounds is exactly the same as the corresponding compound in Tables 1 to 10 (thus, for example, compound 1 of Table 113 is the same as compound 1 of Table 1, compound 663 of Table 113 is the same as compound 1 of Table 2, etc.) except that in all of the compounds of Table 113 Y is CF instead of CH.

Table 114

Table 114 consists of 6620 compounds. Each of these compounds is exactly the same as the corresponding compound in Tables 1 to 10 (thus, for example, compound 1 of Table 114 is the same as compound 1 of Table 1, compound 663 of Table 114 is the same as compound 1 of Table 2, etc.) except that in all of the compounds of Table 114 Y is CCl instead of CH.

Table 115

Table 115 consists of 6620 compounds. Each of these compounds is exactly the same as the corresponding compound in Tables 1 to 10 (thus, for example, compound 1 of Table 115 is the same as compound 1 of Table 1, compound 663 of Table 115 is the same as compound 1 of Table 2, etc.) except that in all of the compounds of Table 115 Y is CBr instead of CH.

Table 116

Table 116 consists of 6620 compounds. Each of these compounds is exactly the same as the corresponding compound in Tables 1 to 10 (thus, for example, compound 1 of Table 116 is the same as compound 1 of Table 1, compound 663 of Table 116 is the same as compound 1 of Table 2, etc.) except that in all of the compounds of Table 116 Y is $CCH_3$ instead of CH.

Table 117

Table 117 consists of 662 compounds of the general formula (1B), where W, X and Z are CH and Y is N, R is Cl, $R^1$ is 2,4,6-trifluorophenyl, and the values of $R^3$ and $R^4$ are as listed in Table 1. Thus, compound 1 of Table 117 is the same as compound 1 of Table 21 except that in compound 1 of Table 117, the compound has the general formula (1B). Similarly, compounds 2 to 662 of Table 117 are the same as compounds 2 to 662 of Table 21 except that in the compounds of Table 117, the compounds have the general formula (1B).

Table 118

Table 118 consists of 662 compounds of the general formula (1B), where W, X and Z are CH and Y is N, R is Cl, $R^1$ is 2,5,6-trifluorophenyl, and the values of $R^3$ and $R^4$ are as listed in Table 1. Thus, compound 1 of Table 118 is the same as compound 1 of Table 22 except that in compound 1 of Table 118, the compound has the general formula (1B). Similarly, compounds 2 to 662 of Table 118 are the same as compounds 2 to 662 of Table 22 except that in the compounds of Table 118, the compounds have the general formula (1B).

Table 119

Table 119 consists of 662 compounds of the general formula (1B), where W, X and Z are CH and Y is N, R is Cl, $R^1$ is 2,3,4,5,6-pentafluorophenyl, and the values of $R^3$ and $R^4$ are as listed in Table 1. Thus, compound 1 of Table 119 is the same as compound 1 of Table 23 except that in compound 1 of Table 119, the compound has the general formula (1B). Similarly, compounds 2 to 662 of Table 119 are the same as compounds 2 to 662 of Table 23 except that in the compounds of Table 119, the compounds have the general formula (1B).

Table 120

Table 120 consists of 662 compounds of the general formula (1B), where W, X and Z are CH and Y is N, R is Cl, $R^1$ is 2,6-difluoro-4-methoxyphenyl, and the values of $R^3$ and $R^4$ are as listed in Table 1. Thus, compound 1 of Table 120 is the same as compound 1 of Table 24 except that in compound 1 of Table 120, the compound has the general formula (1B). Similarly, compounds 2 to 662 of Table 120 are the same as compounds 2 to 662 of Table 24 except that in the compounds of Table 120, the compounds have the general formula (1B).

Table 121

Table 121 consists of 662 compounds of the general formula (1B), where W, X and Z are CH and Y is N, R is Cl, $R^1$ is 2-fluoro-6-chlorophenyl, and the values of $R^3$ and $R^4$ are as listed in Table 1. Thus, compound 1 of Table 121 is the same as compound 1 of Table 25 except that in compound 1 of Table 121, the compound has the general formula (1B). Similarly, compounds 2 to 662 of Table 121 are the same as compounds 2 to 662 of Table 25 except that in the compounds of Table 121, the compounds have the general formula (1B).

Table 122

Table 122 consists of 662 compounds of the general formula (1B), where W, Y and Z are CH and X is N, R is Cl, $R^1$ is 2,4,6-trifluorophenyl, and the values of $R^3$ and $R^1$ are as listed in Table 1. Thus, compound 1 of Table 122 is the same as compound 1 of Table 26 except that in compound 1 of Table 122, the compound has the general formula (1B). Similarly, compounds 2 to 662 of Table 122 are the same as compounds 2 to 662 of Table 26 except that in the compounds of Table 122, the compounds have the general formula (1B).

Table 123

Table 123 consists of 662 compounds of the general formula (1B), where W, Y and Z are CH and X is N, R is Cl, $R^1$ is 2,4,5-trifluorophenyl, and the values of $R^3$ and $R^4$ are as listed in Table 1. Thus, compound 1 of Table 123 is the same as compound 1 of Table 27 except that in compound 1 of Table 123, the compound has the general formula (1B). Similarly, compounds 2 to 662 of Table 123 are the same as compounds 2 to 662 of Table 27 except that in the compounds of Table 123, the compounds have the general formula (1B).

Table 124

Table 124 consists of 662 compounds of the general formula (1B), where W, Y and Z are CH and X is N, R is Cl, $R^1$ is 2,3,4,5,6-pentafluorophenyl, and the values of $R^3$ and $R^4$ are as listed in Table 1. Thus, compound 1 of Table 124 is the same as compound 1 of Table 28 except that in compound 1 of Table 124, the compound has the general formula (1B). Similarly, compounds 2 to 662 of Table 124 are the same as compounds 2 to 662 of Table 28 except that in the compounds of Table 124, the compounds have the general formula (1B).

Table 125

Table 125 consists of 662 compounds of the general formula (1B), where W, Y and Z are CH and X is N, R is Cl, $R^1$ is 2,6-difluoro-4-methoxyphenyl, and the values of $R^3$ and $R^4$ are as listed in Table 1. Thus, compound 1 of Table-125 is the same as compound 1 of Table 29 except that in compound 1 of Table 125, the compound has the general formula (1B). Similarly, compounds 2 to 662 of Table 125 are the same as compounds 2 to 662 of Table 29 except that in the compounds of Table 125, the compounds have the general formula (1B).

Table 126

Table 126 consists of 662 compounds of the general formula (1B), where W, Y and Z are CH and X is N, R is Cl, $R^1$ is 2-fluoro-6-chlorophenyl, and the values of $R^3$ and $R^4$ are as listed in Table 1. Thus, compound 1 of Table 126 is the same as compound 1 of Table 30 except that in compound 1 of Table 126, the compound has the general formula (1B). Similarly, compounds 2 to 662 of Table 126 are the same as compounds 2 to 662 of Table 30 except that in the compounds of Table 126, the compounds have the general formula (1B).

Compounds of formula (7) or (8), which are examples of compounds of general formula (1) where one of R and $R^2$ is $NR^3R^4$, can be made as shown in Scheme 1, in which W, X, Y, Z, $R^1$, $R^3$ and $R^4$ have the meanings given above and $R^7$ is $C_{1-4}$ alkyl.

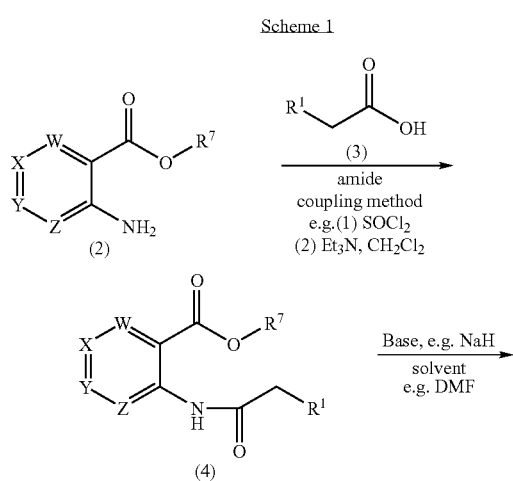

Scheme 1

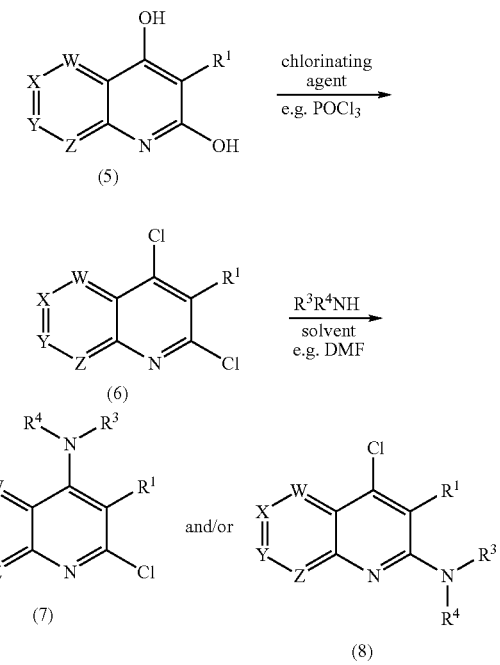

Compounds of general formula (4) can be prepared from compounds of general formula (2), which are either commercially available or made by methods known in the literature, by reaction with acids of general formula (3), using standard coupling methods, for example by conversion to the acid chloride using a chlorinating agent such as thionyl chloride, followed by reaction of the resultant acid chloride optionally in the presence of a base such as triethylamine, in a suitable solvent such as dichloromethane or toluene. Compounds of general formula (5) can be prepared by treating compounds of general formula (4) with a base such as sodium hydride, optionally in the presence of a Lewis acid such as magnesium oxide, in a suitable solvent such as N,N-dimethylformamide (DMF) or toluene, at between room temperature and 150° C., but preferably at 60-90° C. Compounds of general formula (6) can be prepared by reaction of compounds of general formula (5) with a chlorination reagent such as phosphorus oxychloride, either neat or in a suitable solvent such as toluene, at between 50 and 150° C., but preferably between 80 and 110° C., or in a microwave reactor at between 150 and 300° C., but preferably between 200 and 250° C. Compounds of formula (7) and (8) can be prepared by reaction of compounds of general formula (6) with an amine $R^3R^4NH$, either neat, or in a suitable solvent such as DMF, between room temperature and 150° C., but preferably between 50 and 80° C. If compounds (7) and (8) are produced as a mixture they can be separated by suitable means such as crystallisation or chromatography under normal or reverse phase conditions.

Compounds of the general formulae (5), (6), (7) and (8) may be derivatised, via the chloro or hydroxy substituents, using routine chemical techniques to form other compounds of the general formula (1). Alternatively, other compounds of the general formula (1) may be prepared using a similar methodology to that described for preparing the compounds (5) to (8) and employing preparative techniques known from the chemical literature.

Compounds of formula (7) can also be made as shown in scheme 2.

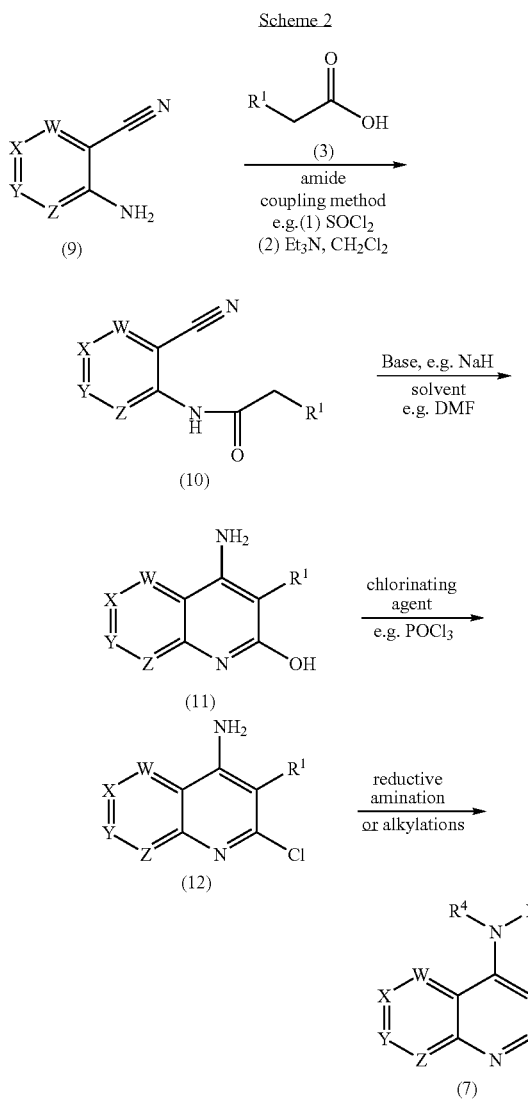

Compounds of general formula (10) can be prepared from compounds of general formula (9), which are either commercially available or made by methods known in the literature, by reaction with acids of general formula (3), using standard coupling methods, for example by conversion to the acid chloride using a chlorinating agent such as thionyl chloride, followed by reaction of the resultant acid chloride optionally in the presence of a base such as triethylamine, in a suitable solvent such as dichloromethane or toluene. Compounds of general formula (11) can be prepared by treating compounds of general formula (10) with a base such as sodium hydride, optionally in the presence of a Lewis acid such as magnesium oxide, in a suitable solvent such as N,N-dimethylformamide (DMF) or toluene, at between room temperature and 150° C., but preferably at 60-90° C. Compounds of general formula (12) can be prepared by reaction of compounds of general formula (11) with a chlorination reagent such as phosphorus oxychloride, either neat or in a suitable solvent such as toluene, at between 50 and 150° C., but preferably between 80 and 110° C., or in a microwave reactor at between 150 and 300° C., but preferably between 200 and 250° C. Compounds of formula (7) can be prepared from compounds of formula (12) by reductive amination, for example by reaction with a ketone or aldehyde in a suitable solvent such as ethanol or toluene, at between room temperature and reflux, optionally in the presence of an acid catalyst such as para-toluenesulphonic acid or a drying agent such as molecular sieves, followed by treatment with a suitable reducing agent such as sodium borohydride, at between −20° C. and 40° C., but preferably at room temperature. The aldehyde or ketone is chosen so that the desired groups $R^3$ and $R^4$ are formed after reduction of the product of reaction with the amine (12). For example if compounds of formula (12) are reacted with one equivalent of propionaldehyde and then sodium borohydride, compounds of formula (7) where $R^3$ is n-propyl, and $R^4$ is hydrogen are formed. If required, the reaction can be repeated with a different aldehyde or ketone. For example, if acetone is used for the second reaction, then compounds of formula (7) where $R^3$ is n-propyl and $R^4$ is iso-propyl, are formed. Alternatively compounds of formula (7) can be formed from compounds of formula (12) by alkylation with a group $R^3LG$, where LG is a leaving group, by treatment with a suitable base such as sodium hydride in a solvent such as DMF, or a base such as potassium carbonate in a solvent such as acetone or DMF, at between −78° C. and 100° C., but preferably between room temperature and 60° C., followed by treatment with $R^4LG$ in a second step under the same conditions if required.

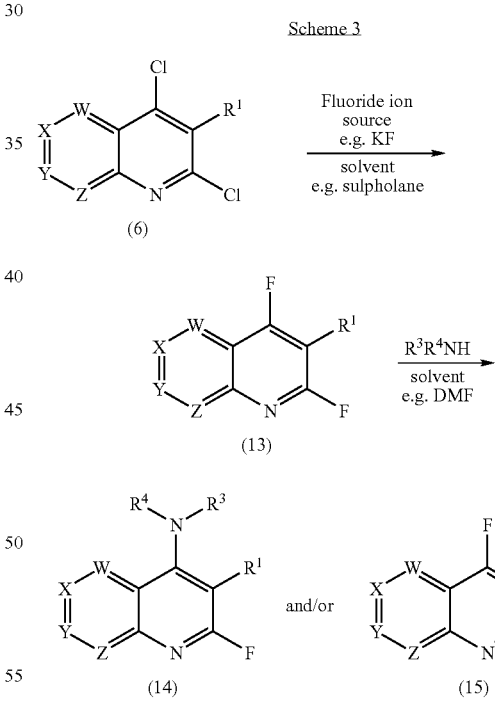

Compounds of formula (13) can be prepared as shown in Scheme 3 from compounds of formula (6) by reaction with a source of fluoride ion, such as potassium fluoride, in a suitable solvent such as sulpholane, at a temperature between 50° C. and 200° C., but preferably at 80-150° C. Compounds of formula (14) and/or compounds of formula (15) can be prepared from difluoro compounds of formula (13) by reaction with an amine of formula $R^3R^4NH$ in a suitable solvent such as DMF or $CH_2Cl_2$, at a temperature of 0° C.-100° C., but preferably at room temperature.

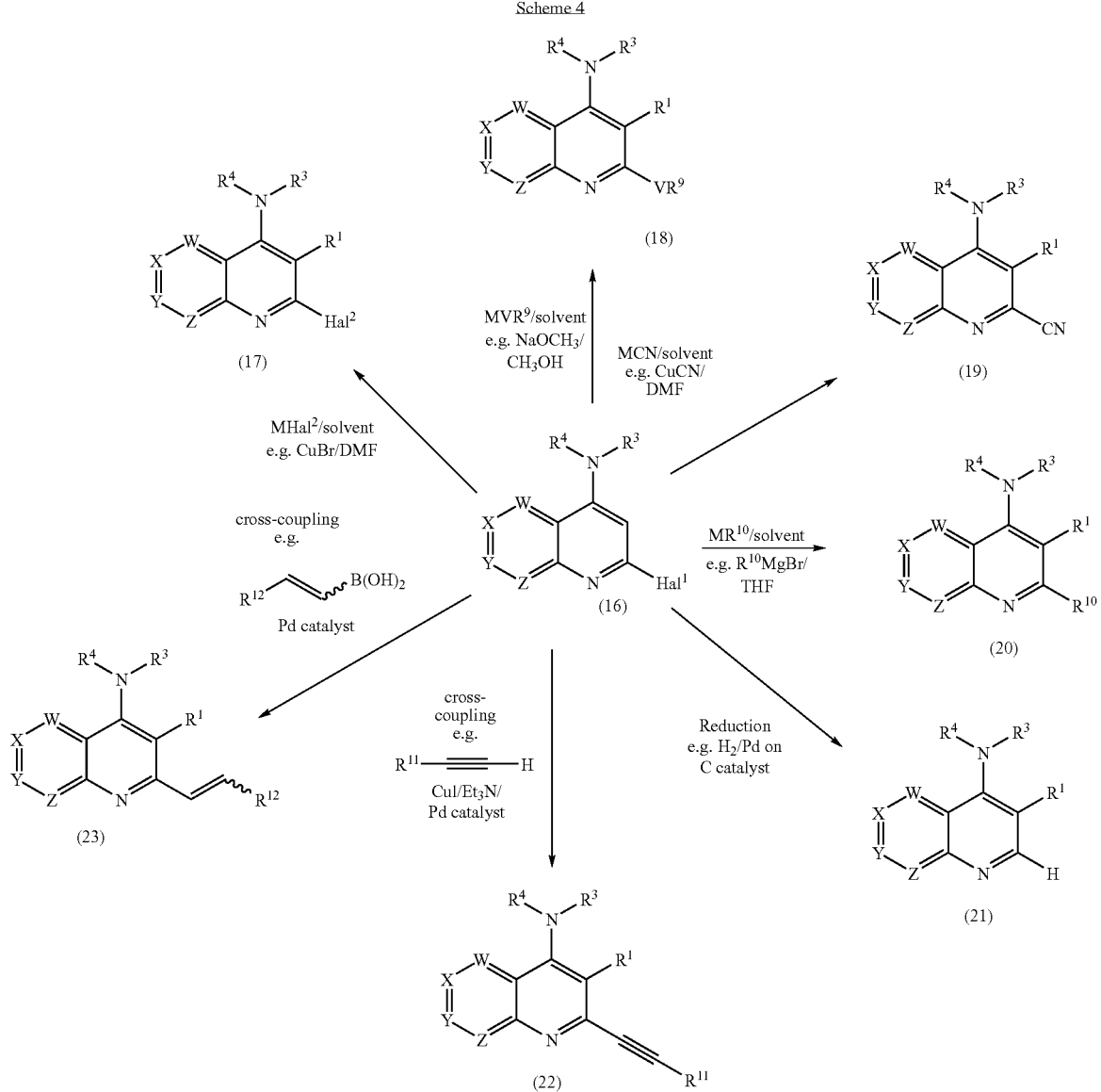

Compounds of general formula (16), where Hal¹ is chlorine or fluorine, can be converted into compounds of formula (17), (18), (19), (20), (21), (22) or (23) as shown in Scheme 4. Compounds of general formula (17) where Hal² is bromine or iodine can be formed by reacting compounds of general formula (16) with a metal halide, for example cuprous bromide, in a suitable solvent, for example DMF, at between room temperature and 155° C., but preferably between 70° C. and 155° C. Compounds of general formula (18) where V is oxygen or sulphur and $R^9$ is $C_{1-8}$ alkyl, can be formed by reacting compounds of general formula (16) with a metal alkoxide or thioalkoxide $MVR^9$ in a suitable solvent, for example sodium methoxide in methanol, at room temperature to 65° C. Compounds of general formula (19) can be formed by reacting compounds of general formula (16) with a metal cyanide in a suitable solvent, for example cuprous cyanide in DMF, at between room temperature and 155° C. but preferably between 50° C. and 155° C. Compounds of general formula (20) where $R^{10}$ is $C_{1-8}$ alkyl, can be formed by reacting compounds of general formula (16) with an alkyl metal derivative in a suitable solvent, for example methyl magnesium bromide in THF, optionally in the presence of catalyst such as cuprous bromide or Pd(Ph)₄, between −40° C. and 50° C. Compounds of general formula (21) can be formed by reduction of compounds of general formula (16), where Hal¹ is chlorine, for example by hydrogenolysis with hydrogen gas and a metal catalyst such as palladium on carbon in a suitable solvent such as ethanol, at room temperature. Compounds of general formula (22) where $R^{11}$ is hydrogen or $C_{1-6}$ alkyl, can be formed by reaction of compounds of general formula (16) with an alkyl acetylene under the Sonogashira conditions, for example with 1-propyne in triethylamine in the presence of a cuprous salt such as cuprous iodide and a palladium catalyst such as Pd(Ph)₄, between room temperature and 70° C. Compounds of general formula (23) where $R^{12}$ is hydrogen or $C_{1-6}$ alkyl, can be formed by reaction of compounds of general formula (16) with an alkenyl metal derivative in a suitable solvent, such as ethenylboronic acid in THF, in the presence of a palladium catalyst such as Pd(Ph)$_4$ and a base such as caesium carbonate, between room temperature and 65° C.

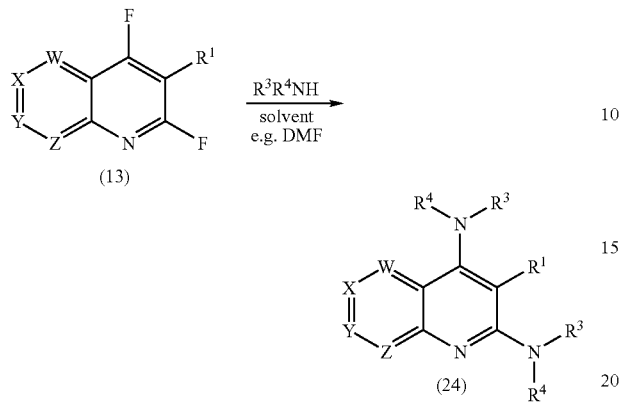

Scheme 5

In Scheme 5 compounds of general formula (24), where the two R$^3$R$^4$N groups are identical, can be made from compounds of general formula (13) by reaction with a large excess of amine R$^3$R$^4$NH in a suitable solvent such as DMF, at a temperature between 0° C. and 150° C., but preferably between room temperature and 100° C.

Further assistance in the preparation of the compounds of formula (1) may be derived from the following publications: Emilio, Toja, et. al., *J. Heterocyclic Chem.*, 23, 1955-(1986), H. Schäfer, et. al., *J. f. prakt. Chemie*, 321(4), 695 (1970) and H. Bredereck et. al., *Chem. Ber.* 96, 1868-1872 (1993).

The intermediate chemicals having the general formulae (4), (5), (6) and (13):

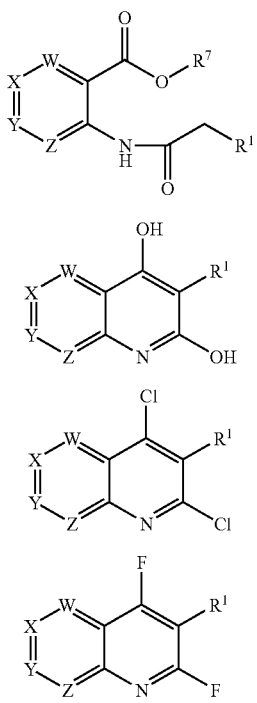

wherein W, X, Y, Z, R$^1$ and R$^7$ are as define above, are believed to be novel compounds and from a further part of this invention.

It should be noted that the intermediate of general formula (5) may exist in the tautomeric forms (a), (b) and (c) as well as in the form shown in formula (5):

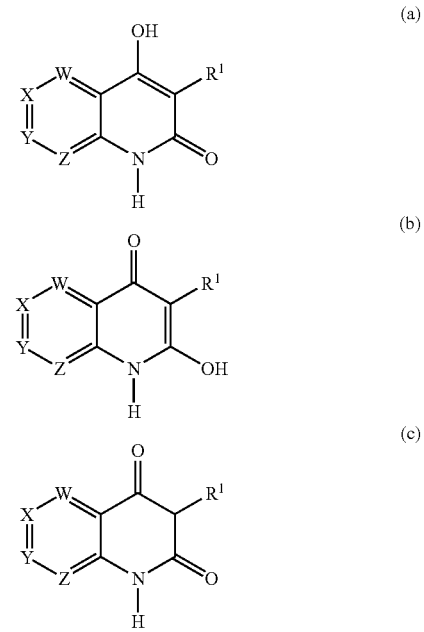

The invention as defined by the general formula (5) embraces all such tautomers.

Of particular interest are the intermediates listed in Tables 127 to 134 below. In Table 127 the compounds have the general formula (4) where R$^7$ is methyl and W, X, Y, Z and R$^1$ have the values shown in the table.

TABLE 127

| Cmpd No. | R$^1$ | W | X | Y | Z |
|---|---|---|---|---|---|
| 1 | 2,4,6-trifluorophenyl | CH | CH | CH | N |
| 2 | 2,5,6-trifluorophenyl | CH | CH | CH | N |
| 3 | 2,3,4,5,6-pentafluorophenyl | CH | CH | CH | N |
| 4 | 2,3,5,6-tetrafluorophenyl | CH | CH | CH | N |
| 5 | 2,6-difluoro-4-methoxyphenyl | CH | CH | CH | N |
| 6 | 2-fluoro-6-chlorophenyl | CH | CH | CH | N |
| 7 | 2,6-difluorophenyl | CH | CH | CH | N |
| 8 | 2,3,5,6-tetrafluorophenyl | CH | CH | CH | N |
| 9 | 2-fluorophenyl | CH | CH | CH | N |
| 10 | 2-chlorophenyl | CH | CH | CH | N |
| 11 | 2-bromophenyl | CH | CH | CH | N |
| 12 | 2,4-dichlorophenyl | CH | CH | CH | N |
| 13 | 2,4,6-trifluorophenyl | N | CH | CH | CH |
| 14 | 2,5,6-trifluorophenyl | N | CH | CH | CH |
| 15 | 2,3,4,5,6-pentafluorophenyl | N | CH | CH | CH |
| 16 | 2,3,5,6-tetrafluorophenyl | N | CH | CH | CH |
| 17 | 2,6-difluoro-4-methoxyphenyl | N | CH | CH | CH |
| 18 | 2-fluoro-6-chlorophenyl | N | CH | CH | CH |
| 19 | 2,6-difluorophenyl | N | CH | CH | CH |
| 20 | 2,3,5,6-tetrafluorophenyl | N | CH | CH | CH |
| 21 | 2-fluorophenyl | N | CH | CH | CH |
| 22 | 2-chlorophenyl | N | CH | CH | CH |
| 23 | 2-bromophenyl | N | CH | CH | CH |
| 24 | 2,4-dichlorophenyl | N | CH | CH | CH |
| 25 | 2,4,6-trifluorophenyl | CH | CH | N | CH |
| 26 | 2,5,6-trifluorophenyl | CH | CH | N | CH |
| 27 | 2,3,4,5,6-pentafluorophenyl | CH | CH | N | CH |

TABLE 127-continued

| Cmpd No. | R¹ | W | X | Y | Z |
|---|---|---|---|---|---|
| 28 | 2,3,5,6-tetrafluorophenyl | CH | CH | N | CH |
| 29 | 2,6-difluoro-4-methoxyphenyl | CH | CH | N | CH |
| 30 | 2-fluoro-6-chlorophenyl | CH | CH | N | CH |
| 31 | 2,6-difluorophenyl | CH | CH | N | CH |
| 32 | 2,3,5,6-tetrafluorophenyl | CH | CH | N | CH |
| 33 | 2-fluorophenyl | CH | CH | N | CH |
| 34 | 2-chlorophenyl | CH | CH | N | CH |
| 35 | 2-bromophenyl | CH | CH | N | CH |
| 36 | 2,4-dichlorophenyl | CH | CH | N | CH |
| 37 | 2,4,6-trifluorophenyl | CH | N | CH | CH |
| 38 | 2,5,6-trifluorophenyl | CH | N | CH | CH |
| 39 | 2,3,4,5,6-pentafluorophenyl | CH | N | CH | CH |
| 40 | 2,3,5,6-tetrafluorophenyl | CH | N | CH | CH |
| 41 | 2,6-difluoro-4-methoxyphenyl | CH | N | CH | CH |
| 42 | 2-fluoro-6-chlorophenyl | CH | N | CH | CH |
| 43 | 2,6-difluorophenyl | CH | N | CH | CH |
| 44 | 2,3,5,6-tetrafluorophenyl | CH | N | CH | CH |
| 45 | 2-fluorophenyl | CH | N | CH | CH |
| 46 | 2-chlorophenyl | CH | N | CH | CH |
| 47 | 2-bromophenyl | CH | N | CH | CH |
| 48 | 2,4-dichlorophenyl | CH | N | CH | CH |

Table 128

Table 128 consists of 48 compounds of the general formula (5), where W, X, Y, Z and R¹ have the values given in Table 127. Thus, compound 1 of Table 128 has the same W, X, Y, Z and R¹ values as compound 1 of Table 127, etc.

Table 129

Table 129 consists of 48 compounds of the general formula (6), where W, X, Y, Z and R¹ have the values given in Table 127. Thus, compound 1 of Table 129 has the same W, X, Y, Z and R¹ values as compound 1 of Table 127, etc.

Table 130

Table 130 consists of 48 compounds of the general formula (13), where W, X, Y, Z and R¹ have the values given in Table 127. Thus, compound 1 of Table 130 has the same W, X, Y, Z and R¹ values as compound 1 of Table 127, etc.

Table 131

Table 131 consists of 48 compounds of the general formula (4), where W, X, Y, Z and R¹ have the values given in Table 127 and R⁷ is ethyl. Thus, compound 1 of Table 131 is the same as compound 1 of Table 127 except that in compound 1 of Table 131, R⁷ is ethyl instead of methyl. Similarly, compounds 2 to 48 of Table 131 are the same as compounds 2 to 48 of Table 127 except that in the compounds of Table 131, R⁷ is ethyl.

The compounds of formula (1) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei*, *Puccinia struiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Montilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmppara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Scierotinia* spp. on turf, peanuts, potatoes, oil-seed rape and other hosts; *Sclerotium* spp. on turf; peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale*, *Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum*, *Penicillium italicum* and *Trichoderma viride* on oranges, *Colletotrichum musae* and *Gloeosporium musarum* on bananas and *Botrytis cinerea* on grapes); other pathogens on vines, notably *Eutypa lata*, *Guignardia bidwellii*, *Phellinus igniarus*, *Phomopsis viticola*, *Pseudopeziza tracleiphila* and *Stereum hirsutum*; other pathogens on trees (for example *Lophodermium seditiosum*) or lumber, notably *Cephaloascus fragrans*, *Ceratocystis* spp., *Ophiostoma piceae*, *Penicillium* spp., *Trichoderma pseudokoningli*, *Trichoderma viride*, *Trichoderma harzianum*, *Aspergillus niger*, *Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings; bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (VP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial-polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-5-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-5-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)—N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metra-fenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, oflurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophps, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipcbnazole, sodium pentachlorophenate, spiroxamine, streptomycin, sulphur, tebuconazole, tecloftalam, tecnazene, tetraconazole, thiabendazole, thifluzamide, 2-(thiocyanomethylthio)-benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

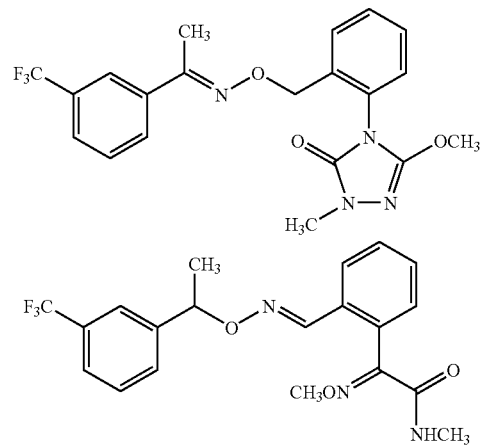

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:
ml=milliliters DCM=dichloromethane
g=grammes DMF=N,N-dinethylformamide
ppm=parts per million DMSO=dimethylsulphoxide
s=singlet DMAP=4-dimethylaminopyridine
d=doublet
t=triplet EDC=1-ethyl-3-N,N-dimethylamino-propylcarbodiimide
q=quartet hydrochloride
m=multiplet NMR=nuclear magnetic resonance
b=broad HPLC=high performance liquid chromatography
f=fine

EXAMPLE 1

This Example illustrates the preparation of [2-chloro-3-(2,4,6-trifluorophenyl)-[1,8]naphthyridin-4-yl]-isopropylamine (Compound No. 3, Table 1) and [4-chloro-3-(2,4,6-trifluorophenyl)-[1,8]naphthyridin-2-yl]-isopropylamine (Compound No. 3, Table 6).

Compound No. 3, Table 1

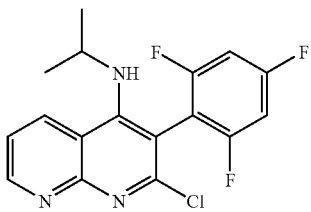

Compound No. 3, Table 6

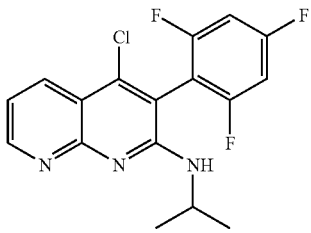

Step 1

2-Aminonicotinic acid ethyl ester (2.4 g) was suspended in dry toluene (50 ml). To the stirred suspension, 2,4,6-trifluorophenylacetyl chloride (3.0 g) in dry toluene (20 ml) was added. The resulting suspension was heated to reflux for 8 hours. The reaction mixture was cooled to ambient temperature, diluted with diethyl ether (100 ml), washed with water and brine, and the organic layer was dried over magnesium sulphate. The solvent was evaporated to give 2-[2-(2,4,6-trifluorophenyl)-acetylamino]-nicotinic acid ethyl ester as a yellow solid (4.5 g, 93%).

$^1$H NMR (CDCl$_3$) δ ppm: 1.33 (t, 3H), 4.00 (s, 2H), 4.31 (q, 2H), 6.63 (m, 2H); 7.00 (dd, 1H), 8.25 (dd, 1H), 8.50 (dd, 1H), 10.86 (s, 1H).

Step 2

The product of Step 1 (3.0 g) was dissolved in toluene (100 ml) and sodium hydride (1.0 g of an 60% dispersion in mineral oil) was added portion-wise. There was an immediate reaction, and the mixture was stirred at room temperature for 2 hours, and at 70° C. for 5 hours. The reaction mixture was cooled and evaporated to give a white solid (3 g), which was then acidified with dilute hydrochloric acid. The resultant white suspension was filtered and collected, washed with ether and dried to give 3-(2,4,6-trifluorophenyl)-1H[1,8]naphthyridine-2,4-dione (1.6 g, 62%).

$^1$H NMR (d$^6$-DMSO) δ ppm: 7.26 (m, 3H), 8.35 (dd, 1H), 8.59 (dd, 1H), 11.21 (s, 1H), 11.97 (s, 1H).

Step 3

The product from Step 2 (1.0 g) was added portion-wise to phosphorus oxychloride (18 ml) with stirring. The reaction was exothermic. The mixture became yellow with a fine suspension, and was then refluxed for 3 hours. Excess phosphorus oxychloride was evaporated, the mixture was diluted with diethyl ether, and then washed with, ice water and brine, and the organic layer was dried over magnesium sulphate. The solvent was evaporated to give 2,4-dichloro-3-(2,4,6-trifluorophenyl)-[1,8]naphthyridine as a yellow solid (1.0 g, 88%).

$^1$H NMR (CDCl$_3$) δ ppm: 6.81 (m, 2H), 7.61 (dd, 1H), 8.60 (dd, 1H), 9.17 (dd, 1H).

Step 4

The product from Step 3 (0.12 g), isopropylamine (0.3 ml) and N-ethyl-diisopropylamine (0.10 g) were refluxed in DMF (8 ml) in a sealed tube at 50° C. for 17 hours. The dark coloured reaction mixture was evaporated to give an oil, which was purified by flash column chromatography on silica gel (40-60, ethyl acetate/hexane 1/3) to give [2-chloro-3-(2,4,6-trifluorophenyl)-[1,8]naphthyridin-4-yl]-isopropylamine as white crystals (0.059 g, 46%), m.p. 193° C.

$^1$H NMR (CDCl$_3$) δ ppm: 1.06 (d, 6H), 3.68 (m, 1H), 4.04 (m, 1H), 6.80 (m, 2H), 7.36 (dd, 1H), 8.28 (dd, 1H), 9.00 (dd, 1H)

and [4-chloro-3-(2,4,6-trifluorophenyl)-[1,8]naphthyridin-2-yl]-isopropylamine as yellow crystals, (0.039 g, 30%), m.p. 202° C.

$^1$H NMR (CDCl$_3$) δ ppm: 1.24 (d, 6H), 4.35 (m, 1H), 4.70 (m, 1H), 6.93 (m, 2H), 7.70 (dd, 1H), 8.38 (dd, 1H), 8.67 (dd, 1H).

EXAMPLE 2

This Example illustrates the preparation of 2-chloro-4-morpholin-4-yl-3-(2,4,6-trifluorophenyl)-[1,8]naphthyridine (Compound No. 20, Table 1).

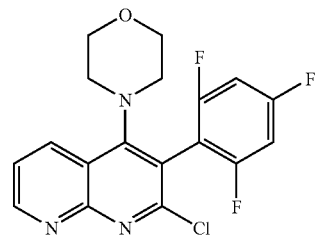

2,4-Dichloro-3-(2,4,6-trifluoro-phenyl)-[1,8]naphthyridine (0.12 g, the product from Example 1, step 3) and morpholine (0.01 ml) were refluxed in DMF (8 ml) in a sealed tube at 50° C. for 17 hours. The dark coloured reaction mixture was evaporated to give an oil, which was purified by flash column chromatography on silica gel (40-60, ethyl acetate/hexane 1/3) to give the title compound as a yellow honey (0.087 g, 63%).

$^1$H NMR (CDCl$_3$) δ ppm: 3.34 (m, 2H), 3.62 (m, 2H), 6.90 (m, 2H), 7.43 (dd, 1H), 8.51 (dd, 1H), 9.05 (dd, 1H).

EXAMPLE 3

This Example illustrates the preparation of [6-bromo-2-chloro-3-(2,4,6-trifluorophenyl)-[1,8]naphthyridin-4-yl]-isopropylamine (Compound No. 3, Table 111).

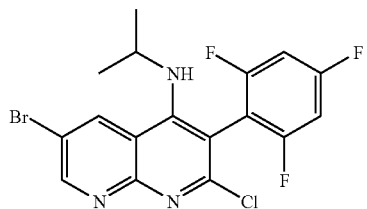

Starting with 2-amino-5-bromo-nicotinic acid ethyl ester using a process analogous to that described in Example 1, steps 1 to 4, the title compound was synthesized (41%), as yellow crystals, m.p. 202° C.
$^1$H NMR (CDCl$_3$) δ ppm: 1.36 (d, 6H), 3.94 (m, 1H), 4.25 (m, 1H), 7.06 (m, 2H), 8.64 (d, 1H), 9.25 (d, 1H).

EXAMPLE 4

This Example illustrates the preparation of [2-chloro-3-(2,4,6-trifluorophenyl)-[1,7]naphthyridin-4-yl]-isopropylamine (Compound No. 3, Table 21), and [4-chloro-3-(2,4,6-trifluoro-phenyl)-[1,7]naphthyridin-2-yl]-isopropylamine (Compound No. 3, Table 117).

Compound No.3, Table 21

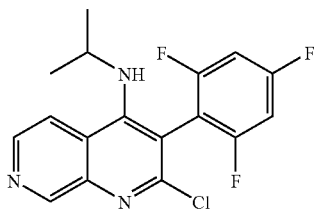

Compound No. 3, Table 117

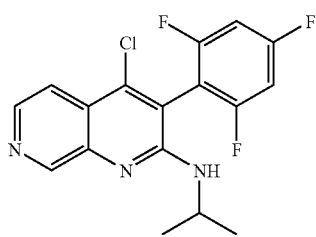

Step 1

3-Amino-4-pyridinecarboxylic acid (5.52 g) was suspended in ethanol (300 ml) at room temperature, with stirring. One equivalent of DMAP (10.0 g) was added initially and the mixture stirred for 1 hour at room temperature to produce a suspension. A second equivalent of DMAP was added and the suspension disappeared. EDC (8.0 g) was then added and the reaction stirred at room temperature for 17 hours. The solvent was removed to give yellow oil, which was water-soluble. The aqueous fraction was extracted with ethyl acetate, washed with brine and dried over magnesium sulphate. After evaporation of the solvent a sludge (16.2 g) was obtained which was passed through a plug of silica gel (40-60) eluting with ethyl acetate, giving a yellow liquid (4.5 g), which by NMR was the desired product ethyl 3-amino-4-pyridinecarboxylate in a ratio of 2:1 with DMAP, and which was used for the next reaction without further purification.
$^1$H NMR (CDCl$_3$) δ ppm: 1.4 (t, 3H), 4.4 (q, 2 h), 5.8 (bs, 2H), 7.6 (d, 1H), 7.95 (d, 1H), 8.2 (s, 1H).

Step 2

The crude ester from Step 1 (4.5 g) was dissolved in dry DCM (30 ml), and then pyridine (5.0 ml) added to give a dark brown solution. The stirred solution was cooled in an ice bath, and 2,4,6-trifluorophenylacetyl chloride (3.1 g) in dry DCM (20 ml) added dropwise. The reaction mixture was stirred for 6 hours and stood over night. The solvent was removed to give an orange sludge, water added and the solid was dissolved in ethyl acetate. The organic fraction was washed with sodium bicarbonate solution, followed by a small amount of 1M hydrochloric acid solution, then water and dried magnesium sulphate. The ethyl acetate was evaporated to yield a solid (6.5 g), which was purified by flash column chromatography on silica gel (40-60), eluting with ethyl acetate to give ethyl 3-[2-(2,4,6-trifluorophenyl)-acetylamino]-pyridine-4-carboxylate as a yellow solid (3.2 g).
$^1$H NMR (CDCl$_3$) δ ppm: 1.45 (t, 3H), 3.8 (fd, 2H), 4.45 (q, 2H) 6.75 (t, 2H), 7.8 (d, 2H), 8.45 (d, 2H), 10.0 (s, 1H), 11.0 (s, 1H).

Step 3

The product from Step 2 (3.0 g) and potassium carbonate (1.6 g) were stirred in dry DMF (100 ml) at 100° C. for 3 hours. The reaction was cooled and the excess DMF evaporated to give a black oil. Water (100 ml) was added and then washed with ethyl acetate. The aqueous fraction was filtered and acidified with 2M aqueous hydrochloric acid to neutral pH, and the water was evaporated to give a solid, which was then extracted with methanol. The methanol extract was evaporated to give the crude 3-(2,4,6-trifluorophenyl)-1H-[1,7]naphthyridine-2,4-dione as a dark brown crystalline solid (2.0 g), which was used for the next reaction without further purification.
$^1$H NMR (CDCl$_3$) δ ppm: 6.8 (t, 2H), 7.95 (m, 2H), 8.2 (d, 1H).

Step 4

The product of Step 3 (0.4 g) was added to phosphorus oxychloride (5.0 ml), and the reaction mixture brought to 85° C. with stirring, and then stirred for 5 hours. The excess phosphorus oxychloride was evaporated to give a brown oil, which was dissolved in diethyl ether (100 ml) and washed with cold water. The ether layer was separated, dried over magnesium sulphate and evaporated to give a sludge (0.150 g), which was purified by flash column chromatography on silica gel (40-60), eluting with diethyl ether, to give 2,4-dichloro-3-(2,4,6-trifluorophenyl)-[1,7]naphthyridine as an oil (0.10 g) which solidified on standing.
$^1$H NMR (CDCl$_3$) δ ppm: 6.9 (t, 2H), 8.05 (d, 1H), 8.8 (d, 1H), 9.5 (s, 1H), M$^+$ 329

Step 5

The product of Step 4 (0.09 g) was dissolved in DCM (3.0 ml) and transferred to a sealed tube containing isopropylamine (1.0 ml), N-ethyl-diisopropylamine (0.07 g) and dimethylacetamide (1.0 ml). The vessel was sealed and gently warmed to 60° C. for 10 hours. The reaction was cooled and evaporated to give an oil, which was purified by flash column chromatography on silica gel (40-60) eluting with diethyl ether. Two isomers were obtained: [2-chloro-3-(2,4,6-trifluoro-phenyl)-[1,7]naphthyridin-4-yl]-isopropylamine as an oil (0.028 g)

¹H NMR (CDCl₃) δ ppm: 1.1 (d, 6H), 3.75 (m, 1H), 4.3 (bd, 1H), 6.9 (t, 2H), 7.75 (d, 1H), 8.6 (d, 1H), 9.35 (s, 1H).

The second isomer, [4-chloro-3-(2,4,6-trifluoro-phenyl)-[1,7]naphthyridin-2-yl]-isopropylamine, was obtained as a mixture with the starting dichloro compound, and was reacted again and purified by chromatography as described above to give the compound as an oil.

¹H NMR (CDCl₃) δ ppm: 1.1 (d, 6H), 4.25 (bd, 1H), 4.5 (m, 1H), 6.9 (t, 2H), 7.75 (d, 1H), 8.4 (d, 1H), 9.15 (s, 1H).

EXAMPLE 5

This Example illustrates the preparation of N-sec-butyl-4-chloro-3-(2-chloro-6-fluorophenyl)-1,6-naphthyridin-2-amine (Compound No. 23, Table 126)

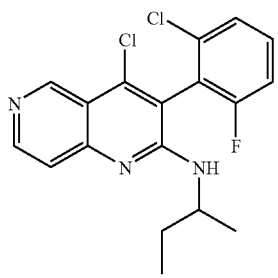

Step 1

Ethyl 4-aminopyridine-3-carboxylate (1.5 g) was dissolved in dry toluene (50 ml) to give a pale yellow solution, and 2-chloro-6-fluorophenylacetyl chloride (1.87 g) in dry DCM (13 ml) was added. The bright yellow reaction mixture was heated at 95° C. for 4 hours. The brownish solution was cooled to ambient temperature, ethyl acetate was added and the mixture was washed with water, brine, and then dilute hydrochloric acid, and the organic layer was dried over magnesium sulphate. The solvent was evaporated to yield a brown solid, which was purified by flash column chromatography on silica gel (40-60) eluting with hexane:ethyl acetate 1:1, to yield pure ethyl 4-(2-(2-chloro-6-fluorophenyl)acetamido)-pyridine-3-carboxylate as a yellow solid (1.4 g), m.p. 114-116° C.

¹H NMR (CDCl₃) δ ppm: 1.32 (t, 3H), 3.91 (s, 2H), 4.28 (q, 2H), 7.02 (m, 1H), 7.21 (m, 2H), 8.51 (m, 2H), 9.07 (s, 1H), 11.2 (s, 1H).

Step 2

The product from Step 1 (1.0 g) was dissolved in DMF (15 ml) and solid potassium carbonate (0.8 g) was added. The resulting pale yellow solution was heated at 100° C. for 4 hours. The reaction mixture was cooled and evaporated to give a yellow solid (3 g), which was then acidified with dilute hydrochloric acid. The resulting white suspension was filtered and collected, washed with ether and dried to give 3-(2-chloro-6-fluorophenyl)-1H-[1,6]naphthyridine-2,4-dione (0.8 g), m.p. 249° C.

¹H NMR (d⁶-DMSO) δ ppm: 6.80 (d, 1H), 7.00 (m, 1H), 7.13 (m, 2H), 8.10 (d, 1H), 8.62 (d, 1H), 12.11 (s, 1H).

Step 3

The product from Step 2 (0.70 g) was dissolved in 1,2-dichloroethane (15 ml). DMF (2 ml) and phosphorus oxychloride (2 ml) were added with stirring. The pale yellow suspension was then refluxed for 4 hours. The reaction mixture was cooled to ambient temperature, diluted with diethyl ether, and then washed with water to give 2,4-dichloro-3-(2-chloro-6-fluorophenyl)-1,6-naphthyridine as a light yellow solid (0.38 g).

H NMR (CDCl₃) δ ppm: 7.12 (td, 1H), 7.32 (d, 1H), 7.41 (d, 1H). 7.87 (bs, 1H), 8.88 (bs, 1H) 9.40 (bs, 1H).

Step 4

The product from Step 3 (0.10 g) was dissolved in DMF (2 ml). Sec-butylamine (0.2 ml) was added and the mixture was refluxed in a sealed tube at 70° C. for 14 hours. The dark coloured reaction mixture was evaporated to give an oil, which was purified by flash column chromatography on silica gel (40-60) in ethyl acetate:hexane 1:1 to give N-sec-butyl-4-chloro-3-(2-chloro-6-fluorophenyl)-1,6-naphthyridin-2-amine as a light yellow gum (0.08 g).

¹H NMR (CDCl₃) δ ppm: 0.08 (m, 3H), 1.10 (t, 3H), 1.48 (m, 2H), 4.18 (m, 1H), 4.28 (m, 1H), 7.10 (m, 1H), 7.36 (t, 1H), 7.40 (m, 1H), 8.52 (d, 1H), 9.20 (s, 1H), 9.30 (s, 1H).

EXAMPLE 6

This Example illustrates the preparation of N-sec-butyl-3-(2-chloro-6-fluorophenyl)-2-fluoro-1,6-naphthyridin-4-amine (Compound No. 19221, Table 103)

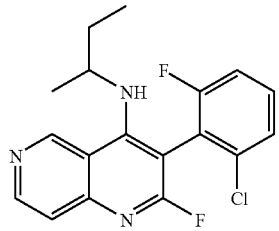

Step 1

2,4-Dichloro-3-(2-chloro-6-fluorophenyl)-1,6-naphthyridine (0.20 g) was dissolved in sulpholane (2 ml). Potassium fluoride (0.11 g) was added and the mixture was heated in a sealed tube at 120° C. for 14 hours. The honey coloured reaction mixture was cooled to ambient temperature, diluted with diethyl ether, and then washed extensively with water. After evaporation of the solvent the resulting light yellow oil was purified by flash column chromatography on silica gel (40-60) eluting with ethyl acetate:hexane 1:4, to give 3-(2-chloro-6-fluorophenyl)-2,4-difluoro-1,6-naphthyridine as a light yellow solid (0.10 g).

¹H NMR (CDCl₃) δ ppm: 7.06 (m, 1H), 7.20 (m, 1H), 7.31 (m, 1H), 8.53 (d, 1H), 9.20 (d, 1H).

Step 6

The product from Step 1 (0.10 g) was dissolved in DMF (2 ml). Sec-butylamine (0.1 ml) and DMAP (0.001 g) were added and the mixture was stirred in a sealed tube at ambient temperature for 18 hours. The brown reaction mixture was diluted with diethyl ether, washed with brine and dried over sodium sulphate. After evaporation of the solvent the resulting yellow gum was purified by flash column chromatography on silica gel (40-60) in ethyl acetate:hexane 1:3 to give N-sec-butyl-3-(2-chloro-6-fluorophenyl)-2-fluoro-1,6-naphthyridin-4-amine as a dark yellow solid (0.06 g).

¹H NMR (CDCl₃) δ ppm: 0.082 (m, 3H), 1.20 (m, 3H), 1.34 (m, 2H), 3.02 (m, 1H), 5.08 (m, 1H), 7.10 (d, 1H), 7.28 (m, 1H), 7.38 (m, 1H), 8.58 (d, 1H), 9.20 (s, 1H), 9.30 (s, 1H).

EXAMPLE 7

This Example illustrates the preparation of [2-chloro-3-(2,4,6-trifluorophenyl)-[1,5]naphthyridin-4-yl]-isopropylamine (Compound No. 3, Table 11)

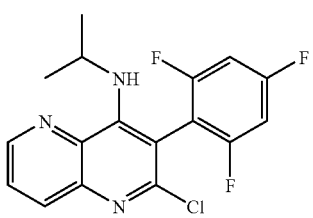

Step 1

3-Amino-2-picolinic acid (4.14 g) was suspended in ethanol (100 ml) at room temperature with stirring. DMAP (3.7 g) was added and the reaction was stirred for 1 hour at room temperature. A further equivalent of DMAP (3.7 g) was added and the suspension disappeared, and then EDC (5.80 g) was added and the reaction was stirred at room temperature for 17 hours. The ethanol was evaporated to give a dark oil, water was added and the mixture was extracted with ethyl acetate, washed with brine and dried over magnesium sulphate. Evaporation of the solvent gave ethyl 3-amino-2-picolinate as a solid (6.5 g), mixed in a 2:1 ratio with DMAP.

$^1$H NMR (CDCl$_3$) δ ppm: 1.4 (t, 3H), 4.45 (q, 2 h), 5.8 (bs, 2H), 7.05 (d, 1H), 7.2 (dd, 1H), 8.05 (fd, 1H).

Step 2

The crude product from Step 1 (6.5 g) was dissolved in dry DCM (150 ml), and triethylamine (5.0 ml) was added to give a dark brown solution. The reaction was stirred in an ice bath, and 2,4,6-trifluorophenylacetyl chloride (8.0 g) in dry DCM (20 ml) was added dropwise. The mixture was stirred for 6 hours and stood for 18 hours. The solvent was evaporated to give an orange sludge, water was added, and the solid was dissolved in ethyl acetate, which was washed with sodium bicarbonate solution and water, and then dried over magnesium sulphate. The ethyl acetate was evaporated to yield a solid (8.5 g), which was purified by flash column chromatography on silica gel (40-60), eluting with ethyl acetate to give a solid which was triturated with diethyl ether to give ethyl 3-[2-(2,4,6-trifluorophenyl)-acetylamino]-pyridine-2-carboxylic acid ethyl ester as a white solid (3.0 g).

$^1$H NMR (CDCl$_3$) δ ppm: 1.45 (t, 3H), 3.85 (d, 2H), 4.5 (q, 2H) 6.75 (t, 2H), 7.5 (m, 1H), 8.45 (d, 2H), 9.0 (d, 1H), 11.2 (s, 1H).

Step 3

The product from Step 2 (0.80 g) and potassium carbonate (0.40 g) were stirred in dry DMF (10 ml) at 100° C. for 6 hours. The reaction mixture was cooled, stood for 18 hours and the DMF was evaporated to give a solid. This was diluted with water (1 ml), acidified to neutrality and the water was evaporated to give a solid, which was then extracted with methanol. The methanol was evaporated to give 3-(2,4,6-trifluorophenyl)-1H-[1,5]naphthyridine-2,4-dione as a peach coloured solid (0.15 g), which was used without further purification.

$^1$H NMR (CD$_3$OD) δ ppm: 6.88 (m, 2H), 7.45 (m, 1H), 7.72 (m, 1H), 8.10 (d, 1H).

Step 4

The product from Step 3 (0.20 g) was added to phosphorus oxychloride (5.0 ml) and the suspension stirred and brought to 85° C. for 5 hours. The phosphorus oxychloride was evaporated to give a brown oil which was dissolved in DCM (100 ml) and washed with cold water. The DCM layer was separated, dried over magnesium sulphate and the solvent was evaporated to give 2,4-dichloro-3-(2,4,6-trifluorophenyl)-[1,5]naphthyridine as a solid (0.070 g).

$^1$H NMR (CDCl$_3$) δ ppm: 6.9 (t, 2H), 7.9 (m, 1H), 8.5 (d, 1H), 9.2 (bs, 1H).

Step 5

The product from Step 4 (0.070 g) was dissolved in isopropylamine (1.0 ml) and warmed in a sealed tube to 60° C. for 2 hours. The isopropylamine was evaporated and the residue was purified by flash column chromatography on silica gel (40-60) eluting with diethyl ether to give [2-chloro-3-(2,4,6-trifluorophenyl)-[1,5]naphthyridin-4-yl]-isopropylamine as a yellow gum (0.009 g).

$^1$H NMR (CDCl$_3$) δ ppm: 1.1 (d, 6H), 3.25 (m, 1H), 6.8 (t, 2H), 7.6 (dd, 1H), 8.35 (d, 1H), 8.7 (d, 1H).

TABLE 132

| Compound No. | Table No. | Compound Structure | NMR data (ppm, in CDCl$_3$, unless otherwise stated) or Mpt. |
| --- | --- | --- | --- |
| 3 | 1 | 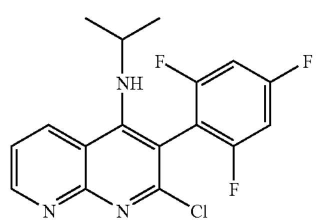 | 1.06(d, 6H), 3.68(m, 1H), 4.04(m, 1H), 6.80(m, 2H), 7.36(dd, 1H), 8.28(dd, 1H), 9.00(dd, 1H) |
| 20 | 1 | 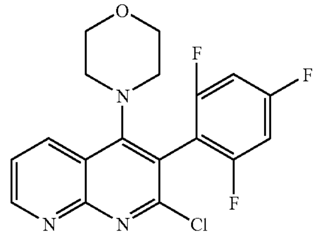 | 3.34(m, 2H), 3.62(m, 2H), 6.90(m, 2H), 7.43(dd, 1H), 8.51(dd, 1H), 9.05(dd, 1H) |

TABLE 132-continued

| Compound No. | Table No. | Compound Structure | NMR data (ppm, in CDCl₃, unless otherwise stated) or Mpt. |
|---|---|---|---|
| 3 | 6 | | 1.24(d, 6H), 4.35(m, 1H), 4.70(m, 1H), 6.93(m, 2H), 7.70(dd, 1H), 8.38(dd, 1H), 8.67(dd, 1H). |
| 3 | 11 | | 1.1(d, 6H), 3.25(m, 1H), 6.8(t, 2H), 7.6(dd, 1H), 8.35(d, 1H), 8.7(d, 1H). |
| 3 | 21 | | 1.1(d, 6H), 3.75(m, 1H), 4.3(bd, 1H), 6.9(t, 2H), 7.75(d, 1H), 8.6(d, 1H), 9.35(s, 1H). |
| 19221 | 103 | 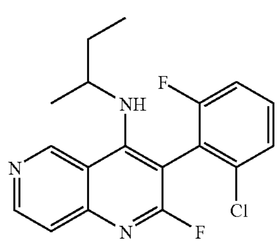 | 0.082(m, 3H), 1.20(m, 3H), 1.34(m, 2H), 3.02(m, 1H), 5.08(m, 1H), 7.10(d, 1H), 7.28(m, 1H), 7.38(m, 1H), 8.58(d, 1H), 9.20(s, 1H), 9.30(s, 1H). |
| 3 | 111 | | 1.36(d, 6H), 3.94(m, 1H), 4.25(m, 1H), 7.06(m, 2H), 8.64(d, 1H), 9.25(d, 1H). |
| 3313 | 111 | 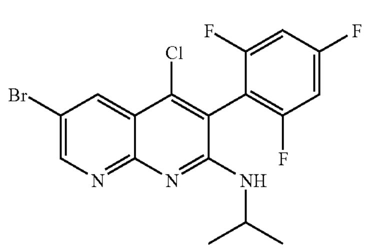 | 165-166° C. |

TABLE 132-continued

| Compound No. | Table No. | Compound Structure | NMR data (ppm, in CDCl₃, unless otherwise stated) or Mpt. |
|---|---|---|---|
| 3 | 117 | 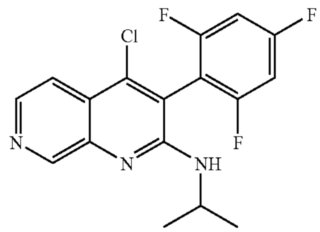 | 1.1(d, 6H), 4.25(bd, 1H), 4.5(m, 1H), 6.9(t, 2H), 7.75(d, 1H), 8.4(d, 1H), 9.15(s, 1H). |
| 23 | 126 | 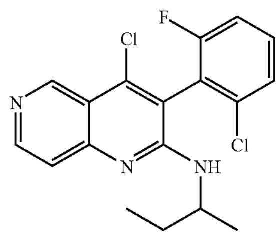 | 0.08(m, 3H), 1.10(t, 3H), 1.48(m, 2H), 4.18(m, 1H), 4.28(m, 1H), 7.10(m, 1H), 7.36(t, 1H), 7.40(m, 1H), 8.52(d, 1H), 9.20(s, 1H), 9.30(s, 1H). |
| 1 | 131 | | 1.33(t, 3H), 4.00(s, 2H), 4.31(q, 2H), 6.63(m, 2H); 7.00(dd, 1H), 8.25(dd, 1H), 8.50(dd, 1H), 10.86(s, 1H). |
| 13 | 131 | 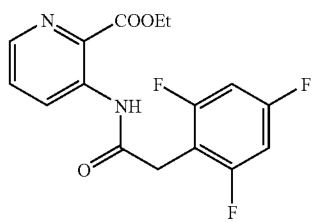 | 1.45(t, 3H), 3.85(d, 2H), 4.5(q, 2H), 6.75(t, 2H), 7.5(m, 1H), 8.45(d, 2H), 9.0(d, 1H), 11.2(s, 1H). |
| 25 | 131 | 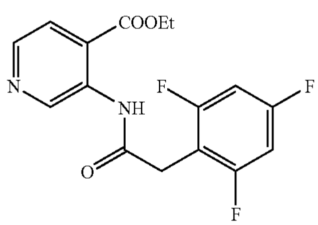 | 1.45(t, 3H), 3.8(fd, 2H), 4.45(q, 2H) 6.75(t, 2H), 7.8(d, 2H), 8.45(d, 2H), 10.0(s, 1H), 11.0(s, 1H). |
| 42 | 131 | 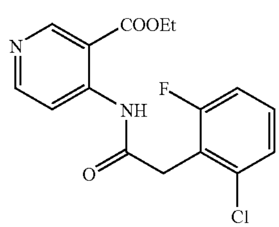 | 114-116° C. |
| 1 | 128 | | 7.26(m, 3H), 8.35(dd, 1H), 8.59(dd, 1H), 11.21(s, 2H), 11.97(s, 1H). |

TABLE 132-continued

| Compound No. | Table No. | Compound Structure | NMR data (ppm, in CDCl₃, unless otherwise stated) or Mpt. |
|---|---|---|---|
| 13 | 128 | | 6.88(m, 2H), 7.45(m, 1H), 7.72(m, 1H), 8.10(d, 1H). |
| 25 | 128 | | 6.8(t, 2H), 7.95(m, 2H), 8.2(d, 1H). |
| 42 | 128 | | 249° C. |
| 1 | 129 | 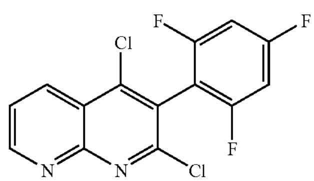 | 151-153° C. |
| 13 | 129 | | 6.9(t, 2H), 7.9(m, 1H), 8.5(d, 1H), 9.2(bs, 1H). |
| 25 | 129 | | 6.9(t, 2H), 8.05(d, 1H), 8.8(d, 1H), 9.5(s, 1H) |
| 42 | 129 | | 7.12(td, 1H), 7.32(d, 1H), 7.41(dd, 1H), 7.87(bs, 1H), 8.88(bs, 1H) 9.40(bs, 1H). |
| 42 | 130 | | 7.06(m, 1H), 7.20(m, 1H), 7.31(m, 1H), 8.53(d, 1H), 9.20(d, 1H) |

EXAMPLE 8

This Example illustrates the fungicidal properties of the compounds of the general formula (1).

Compounds were tested in a leaf disk assay, with methods described below. Test compounds were dissolved in DMSO, and diluted into water to 200 ppm.

*Erysiphe graminis* f. sp. *hordei* (barley powdery mildew): barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f. sp. *tritici* (wheat powdery mildew): wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f. sp. *tritici* (wheat brown rust): wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Pyncularia oryzae* (rice blast): rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): grapevine leaf disks were placed on agar in a 24 well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

The following compounds gave greater than 60% control of disease:

*Plasmopara viticola*, Compounds 3 (111);
*Phytophthora infestans*, Compounds 20 (1);
*Erysiphe graminis* f. sp. *hordei*, Compounds 3 (1), 20 (1), 3 (111);
*Erysiphe graminis* f. sp. *tritici*, Compounds 3 (1), 3 (11), 3 (21);
*Puccinia recondita* f. sp. *tritici*, Compounds 3 (1), 3 (117);
*Pyricularia oryzae*, Compounds 3 (1), 20 (1), 3 (21);
*Botrytis cinerea*, Compounds 3 (1).

The invention claimed is:
1. The compound of the general formula (1):

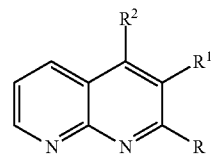

wherein
R is halo;
$R^1$ is aryl or heteroaryl;
$R^2$ is $NR^3R^4$,
   wherein $R^3$ and $R^4$ are independently H, $C_{1-8}$ alkyl, $C_{2-8}$ alkenyl, $C_{2-8}$ alkynyl,
   or wherein $R^3$ and $R^4$ together form a $C_{3-7}$ alkylene or $C_{3-7}$ alkenylene chain optionally substituted with one or more $C_{1-4}$ alkyl or $C_{1-4}$ alkoxy groups;
   or wherein $R^3$ and $R^4$ together with the nitrogen atom to which they are attached form a morpholine, thiomorpholine, thiomorpholine S-oxide or thiomorpholine S-dioxide ring or a piperazine or piperazine N—$(C_{1-4})$alkyl ring;
and wherein
said alkyl, alkenyl, or alkynyl groups are optionally substituted with halogen, cyano, $C_{1-6}$alkoxy, $C_{1-6}$alkylcarbonyl, $C_{1-6}$alkoxycarbonyl, $C_{1-6}$haloalkoxy, $C_{1-6}$alkylthio, tri$(C_{1-4})$alkylsilyl, $C_{1-6}$alkylamino or $C_{1-6}$dialkylamino;
said morpholine, thiomorpholine, and piperazine rings are optionally substituted with $C_{1-4}$ alkyl; and
said aryl or heteroaryl groups are optionally substituted with one or more substituents selected from the group consisting halo, hydroxy, mercapto, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, halo$(C_{1-6})$alkyl, halo$(C_{1-6})$alkoxy, $C_{1-6}$alkylthio, halo$(C_{1-6})$alkylthio, hydroxy$(C_{1-6})$alkyl, $C_{1-4}$alkoxy$(C_{1-6})$alkyl, $C_{3-6}$cycloalkyl, $C_{3-6}$cycloalkyl$(C_{1-4})$alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR''' and —N=CR'''R'''', in which R''' and R'''' are independently hydrogen, $C_{1-4}$ alkyl, halo$(C_{1-4})$alkyl, $C_{1-4}$ alkoxy, halo$(C_{1-4})$alkoxy, $C_{1-4}$ alkylthio, $C_{3-6}$ cycloalkyl, $C_{3-6}$ cycloalkyl$(C_{1-4})$ alkyl, phenyl or benzyl, the phenyl and benzyl groups being optionally substituted with halogen, $C_{1-4}$ alkyl or $C_{1-4}$ alkoxy.

2. A compound according claim 1 wherein:
(A) $R^3$ is $C_{1-8}$ alkyl, halo$(C_{1-8})$ alkyl, hydroxy$(C_{1-8})$alkyl, $C_{1-4}$ alkoxy$(C_{1-8})$alkyl, $C_{1-4}$ alkoxyhalo$(C_{1-8})$alkyl, tri$(C_{1-4})$alkylsilyl$(C_{1-6})$alkyl, $C_{1-4}$ alkylcarbonyl$(C_{1-8})$alkyl, $C_{1-4}$ alkylcarbonylhalo$(C_{1-8})$alkyl, phenyl$(_{1-4})$alkyl, $C_{2-8}$ alkenyl, halo$(C_{2-8})$alkenyl, $C_{2-8}$ alkynyl; and $R^4$ is H, $C_{1-4}$ alkyl, halo$(C_{1-4})$alkyl or amino; or
(B) $R^3$ and $R^4$ together form a $C_{3-7}$ alkylene or $C_{3-7}$ alkenylene chain optionally substituted with methyl; or
(C) $R^3$ and $R^4$, together with the nitrogen atom to which they are attached, form a morpholine, thiomorpholine, piperazine or piperazine N—($C_{1-4}$)alkyl ring, in which the morpholine or piperazine rings are optionally substituted with methyl.

3. A compound according to claim 1 wherein $R^1$ is phenyl optionally substituted with from one to five halogen atoms or with from one to three substituents selected from halo, $C_{1-4}$ alkyl, halo($C_{1-4}$)alkyl, $C_{1-4}$ alkoxy or halo($C_{1-4}$)alkoxy.

4. A compound according to claim 3 wherein $R^1$ is 2,6-difluorophenyl, 2-fluoro-6-chlorophenyl, 2,5,6-trifluorophenyl, 2,4,6-trifluorophenyl, 2,6-difluoro-4-methoxyphenyl or pentafluorophenyl.

5. A compound according to claim 1 wherein:
(A) $R^3$ is $C_{1-8}$ alkyl, halo($C_{1-4}$)alkyl, $C_{2-4}$ alkenyl; and $R^4$ is H, or $C_{1-4}$ alkyl;
(B) or wherein $R^3$ and $R^4$ together form a $C_{3-7}$ alkylene chain optionally substituted with $C_{1-4}$ alkyl;
(C) or wherein $R^3$ and $R^4$, together with the nitrogen atom to which they are attached, form a morpholine, piperazine or piperazine N—($C_{1-4}$)alkyl ring; and
wherein said alkyl or alkenyl groups are optionally substituted with halogen, cyano, $C_{1-6}$ alkoxy, $C_{1-6}$alkylcarbonyl, $C_{1-6}$ alkoxycarbonyl, $C_{1-6}$ haloalkoxy, $C_{1-6}$ alkylthio, tri($C_{1-4}$)alkylsilyl, $C_{1-6}$ alkylamino or $C_{1-6}$dialkylamino;
and wherein said morpholine and piperazine rings are optionally substituted with $C_{1-4}$ alkyl;
and wherein said aryl groups are optionally substituted with one or more substituents selected from the group consisting of halo, hydroxy, mercapto, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$alkynyloxy, halo($C_{1-6}$)alkyl, halo($C_{1-6}$)alkoxy, $C_{1-6}$ alkylthio, halo($C_{1-6}$)alkylthio, hydroxy($C_{1-6}$)alkyl, $C_{1-4}$ alkoxy($C_{1-6}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R'''', —NHCOR''', —NHCONR'''R'''', —CONR'''R'''', —SO$_2$R''', —OSO$_2$R''', —COR''', —CR'''=NR''' and —N=CR'''R'''' in which R''' and R'''' are independently hydrogen, $C_{1-4}$alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

6. A compound according to claim 1 wherein $R^1$ is optionally substituted phenyl.

7. A compound according to claim 1 wherein:
$R^1$ is phenyl optionally substituted with from one to five halogen atoms or with from one to three substituents selected from the group consisting of halo, $C_{1-4}$ alkyl, halo($C_{1-4}$)alkyl, $C_{1-4}$alkoxy and halo($C_{1-4}$)alkoxy; and
wherein $R^3$ is $C_{1-4}$ alkyl or halo($C_{1-4}$) alkyl; and $R^4$ is H;
or wherein $R^3$ and $R^4$ together form a $C_{4-6}$ alkylene chain optionally substituted with methyl;
or wherein $R^3$ and $R^4$ together with the nitrogen atom to which they are attached, form a morpholine or piperazine N—($C_{1-4}$)alkyl ring, in which the morpholine or piperazine rings are optionally substituted with methyl.

8. A compound according to claim 1 wherein:
$R^1$ is phenyl optionally substituted with from one to five halogen atoms; and
wherein $R^3$ is $C_{1-4}$ alkyl; and $R^4$ is H;
or wherein $R^3$ and $R^4$ together form a $C_{4-6}$ alkylene chain optionally substituted with methyl;
or wherein $R^3$ and $R^4$, together with the nitrogen atom to which they are attached, form a morpholine ring.

9. A process for preparing a compound of the general formula (I) according to claim 1 wherein R is chloro or fluoro, comprising:
(A) reacting an amine of the general formula $NR^3R^4$ with a compound of the general formula (6) or (13):

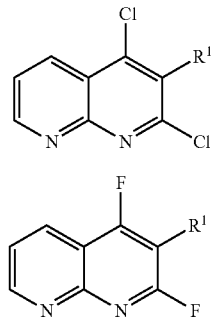

wherein $R^1$, $R^3$ and $R^4$ are as defined in claim 1.

10. A plant fungicidal composition comprising a fungicidally effective amount of a compound as defined in claim 1 and a suitable carrier or diluent therefor.

11. A method of combating or controlling phytopathogenic fungi which comprises applying to a plant, to a seed of a plant, to the locus of the plant or seed or to soil, a fungicidally effective amount of a compound according to claim 1.

* * * * *